US008569416B2

(12) United States Patent
Evans et al.

(10) Patent No.: US 8,569,416 B2
(45) Date of Patent: *Oct. 29, 2013

(54) SINGLE PHASE SILICONE ACRYLATE FORMULATION

(75) Inventors: Chana Wilson Evans, Saginaw, MI (US); Robert O. Huber, Midland, MI (US); David P. Kanios, Palmetto Bay, FL (US); Gary Lee Loubert, Saginaw, MI (US); Tiffany Anne Menjoulet, Clare, MI (US); Timothy Paul Mitchell, Clio, MI (US); Linda Sue Nartker, Midland, MI (US); Xavier Jean-Paul Thomas, Famars (FR)

(73) Assignees: Dow Corning Corporation, Midland, MI (US); Dow Corning France SAS, Lyon Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/278,979

(22) Filed: Oct. 21, 2011

(65) Prior Publication Data

US 2012/0108560 A1 May 3, 2012

Related U.S. Application Data

(63) Continuation-in-part of application No. 12/303,362, filed as application No. PCT/US2007/013321 on Jun. 6, 2007, now Pat. No. 8,124,689.

(60) Provisional application No. 60/811,246, filed on Jun. 6, 2006.

(51) Int. Cl.
*C08L 83/10* (2006.01)
*A61K 9/70* (2006.01)

(52) U.S. Cl.
USPC ........... 525/100; 525/477; 526/319; 526/328; 528/24; 528/25; 528/34; 528/38; 424/447; 424/448; 424/484; 424/486

(58) Field of Classification Search
None
See application file for complete search history.

(56) References Cited

U.S. PATENT DOCUMENTS

| | | | |
|---|---|---|---|
| 2,490,357 A | 12/1949 | Hyde | |
| 2,542,334 A | 2/1951 | Hyde | |
| 2,736,721 A | 2/1956 | Dexter | |
| 2,814,601 A | 11/1957 | Currie et al. | |
| 2,857,356 A | 10/1958 | Goodwin, Jr. | |
| 2,927,907 A | 3/1960 | Polmanteer | |
| RE24,906 E | 12/1960 | Ulrich | |
| 3,002,951 A | 10/1961 | Johannson | |
| 3,161,644 A | 12/1964 | Janssen | |
| 3,186,967 A | 6/1965 | Nitzsche et al. | |
| 3,509,191 A | 4/1970 | Atwel | |
| 3,528,940 A | 9/1970 | Modie | |
| 3,697,473 A | 10/1972 | Polmanteer et al. | |
| 3,731,683 A | 5/1973 | Zaffaroni | |
| 3,797,494 A | 3/1974 | Zaffaroni | |
| 4,031,894 A | 6/1977 | Urquhart et al. | |
| 4,336,243 A | 6/1982 | Sanvordeker et al. | |
| 4,618,644 A | 10/1986 | Liu | |
| 4,655,767 A | 4/1987 | Woodard et al. | |
| 4,791,163 A | 12/1988 | Traver et al. | |
| 5,063,254 A | 11/1991 | Nakos | |
| 5,308,887 A | 5/1994 | Ko et al. | |
| 5,418,016 A | 5/1995 | Cornforth et al. | |
| 5,464,659 A | 11/1995 | Melancon et al. | |
| 5,474,783 A | 12/1995 | Miranda et al. | |
| 5,624,763 A | 4/1997 | Melancon et al. | |
| 5,656,286 A | 8/1997 | Miranda et al. | |
| 5,965,154 A | 10/1999 | Haralambopoulos | |
| 5,982,041 A | 11/1999 | Mitani et al. | |
| 6,024,976 A | 2/2000 | Miranda et al. | |
| 6,221,383 B1 | 4/2001 | Miranda et al. | |
| 6,235,306 B1 | 5/2001 | Miranda et al. | |
| 6,337,086 B1 | 1/2002 | Kanios et al. | |
| 6,387,487 B1 | 5/2002 | Greenberg et al. | |
| 6,465,004 B1 | 10/2002 | Rossi-Montero et al. | |
| 6,638,528 B1 | 10/2003 | Kanios | |
| 8,124,689 B2 | 2/2012 | Loubert et al. | |
| 2002/0168401 A1 | 11/2002 | Kanios et al. | |
| 2006/0034905 A1 | 2/2006 | Singh et al. | |
| 2008/0300358 A1 | 12/2008 | Cook et al. | |

(Continued)

FOREIGN PATENT DOCUMENTS

EP 0278618 A2 8/1988
EP 289929 A2 11/1988

(Continued)

OTHER PUBLICATIONS

English language abstract for JP 62295982 extracted from espacenet.com database, dated Apr. 28, 2009.
English language abstract for JP 63291971 extracted from espacenet.com database, dated Jun. 23, 2009.
PCT International Search Report for PCT/US2007/013321 dated May 7, 2008, 9 pages.
Article: Chien et al., "Novel Drug Delivery System—Drugs and the Pharmaceutical Sciences", 1982, vol. 14, pp. 149-217.
Article: Bartell, "Chapter 19—Saturated Paper and Saturated Paper Tapes", Handbook of Pressure-Sensitive Adhesive Technology, 1982, pp. 404-418.
Article: Fukuzawa et al. "Chapter 21—Packaging Tapes", Handbook of Pressure-Sensitive Adhesive Technology, 1982, pp. 426-437.

(Continued)

*Primary Examiner* — Marc Zimmer
(74) *Attorney, Agent, or Firm* — Howard & Howard Attorneys PLLC

(57) ABSTRACT

This invention provides a single phase silicone acrylate formulation that resists phase separation and includes (A) at least one of a silicone, an acrylate, and combinations thereof. The single phase silicone acrylate formulation also includes (B) a silicone acrylate hybrid compatibilizing agent including silicone functionality and (meth)acrylate functionality and that is the reaction product of a silicon-containing pressure sensitive adhesive composition, a (meth)acrylate, and an initiator. A method of minimizing phase separation of the single phase silicone acrylate formulation includes the step of combining (A) and (B) to form the single phase silicone acrylate formulation.

30 Claims, No Drawings

(56) References Cited

U.S. PATENT DOCUMENTS

| | | |
|---|---|---|
| 2009/0048124 A1 | 2/2009 | Leamon et al. |
| 2009/0196911 A1* | 8/2009 | Loubert et al. ............... 424/449 |
| 2012/0114737 A1 | 5/2012 | Loubert et al. |

FOREIGN PATENT DOCUMENTS

| | | |
|---|---|---|
| EP | 0429222 A1 | 5/1991 |
| EP | 1002846 A1 | 5/2000 |
| EP | 1025843 A2 | 8/2000 |
| EP | 1076081 A1 | 2/2001 |
| JP | 62295982 A | 12/1987 |
| JP | 63291971 A | 11/1988 |
| WO | WO 9216591 A1 | 10/1992 |
| WO | WO 9216593 A2 | 10/1992 |
| WO | WO 9220751 A1 | 11/1992 |
| WO | WO 9220752 A1 | 11/1992 |
| WO | WO 9639458 A1 | 12/1996 |
| WO | WO 02077287 A1 | 10/2002 |
| WO | WO 2007050580 A2 | 5/2007 |
| WO | WO 2007/145996 A2 | 12/2007 |
| WO | WO 2010/124187 A2 | 10/2010 |

OTHER PUBLICATIONS

Article: Odian, Principles of Polymerization, Wiley-Interscience, 4th Edition, 2004, pp. 198-332.

Article: Auchter et al., "Chapter 19—Acrylic Adhesives", Handbook of Pressure-Sensitive Adhesive Technology, 1999, pp. 444-514.

Article: Jones, "Chapter 21—Silicone Pressure Sensitive Adhesives", Handbook of Pressure-Sensitive Adhesive Technology, 1999, pp. 550-559.

European Search Report for Application No. EP 12 18 9221 dated Jan. 16, 2013, 2 pages.

European Search Report for Application No. EP 12 19 4816 completed on Mar. 12, 2013; 2 pages.

* cited by examiner

SINGLE PHASE SILICONE ACRYLATE FORMULATION

RELATED APPLICATIONS

This application is a continuation-in-part of, and claims priority to, U.S. Ser. No. 12/303,362, filed on Dec. 3, 2008, which claims priority to and all the advantages of International Patent Application No. PCT/US2007/013321, filed on Jun. 6, 2007, which claims priority to U.S. Provisional Patent Application No. 60/811,246, filed on Jun. 6, 2006.

FIELD OF THE INVENTION

The present invention generally relates to a single phase silicone acrylate formulation and a method of reducing phase separation of the single phase silicone acrylate formulation. More specifically, the single phase silicone acrylate formulation includes a silicone acrylate hybrid compatibilizing agent that is the reaction product of a silicon-containing pressure sensitive adhesive composition, a (meth)acrylate monomer, and an initiator.

BACKGROUND OF THE INVENTION

Pressure sensitive adhesives, also referred to as "PSAs", are known in the art and are commercially available. Some of the more common types of PSAs are formulations based on acrylates, polyurethanes, natural rubbers, synthetic rubbers, and silicones. These PSAs are typically formulated for end use and find utility in a wide variety of applications including tapes, labels, bandages, transdermal drug delivery systems (e.g. patches), laminating adhesives, and transfer adhesives.

Acrylate-based PSAs, also referred to throughout as acrylate PSAs, are broadly used in these applications due to the fact that they are relatively low in cost when compared to other PSAs, solubilize many types of functional drugs for transdermal patches, adhere well to a variety of different surfaces, and can be formulated to build adhesion to a surface, if necessary. The disadvantages of acrylate-based PSAs include poor high temperature performance, poor low temperature performance, inability to adhere to surfaces with low surface energies, and the potential to build excessive adhesion to the skin in medical tape applications which can result in painful removal for the user. Examples of such acrylate-based PSAs are disclosed in U.S. Pat. No. RE 24,906.

Silicone-based PSAs, also referred to throughout as silicone PSAs, are typically produced by either blending or condensing together a silicone resin and a silicone polymer, such as polydimethylsiloxane (PDMS). Silicone materials by nature are very stable at high temperatures and the low glass transition temperature (Tg) of PDMS (less than −115° C.) ultimately provides a PSA that can find use in temperatures ranging from −100° C. to 265° C. Silicone-based PSAs also have excellent chemical inertness, electrical insulating properties, biocompatibility, and the ability to adhere to low surface energy substrates such as silicone release liners, polytetrafluoroethylene, and fluorohalocarbon materials. The primary disadvantage of silicone-based PSAs is their high cost compared to other technologies. Other limitations include lower tack and limited adhesion build (when necessary) in comparison to acrylate-based PSAs. Examples of such silicone-based PSAs are disclosed in U.S. Pat. Nos. 2,736,721; 2,814,601; 2,857,356; and 3,528,940.

There have been many attempts to combine acrylate PSAs and silicone PSAs to gain the advantages of both technologies. As a more specific example of one particular application, silicone pressure sensitive adhesives are frequently applied in the transdermal drug delivery systems. As is known, these systems typically include an active agent and the silicone pressure sensitive adhesive. The active agent, for example a pharmaceutical drug, is for controlled transdermal delivery or release to a substrate, such as the skin of a user of the system. The pressure sensitive adhesive functions to maintain contact between the system and the substrate for extended periods of time such that the active agent can be delivered to the substrate. Examples of such systems can be found in U.S. Pat. Nos. 3,731,683; 3,797,494; 4,031,894; and 4,336,243. Due to the particular silicone pressure sensitive adhesives used, the transdermal drug delivery systems of this prior art do not sufficiently optimize the solubility of the active agent in the pressure sensitive adhesives. As a result, the rate at which the active agent is released from the system for delivery to the substrate and also the total amount of the active agent that is ultimately released and delivered to the substrate are not optimized in this prior art.

In U.S. Pat. Nos. 5,474,783; 5,656,286; 6,024,976; 6,221,383; 6,235,306; 6,465,004; and 6,638,528, all to Noven Pharmaceuticals, Inc., the solubility of an active agent in a transdermal drug delivery system is optimized by simply blending acrylate pressure sensitive adhesives and silicone pressure sensitive adhesives together in varying ratios. However, because the two, separate PSAs are not actually chemically reacted together, domains of one PSA form within the continuous phase of the other PSA. In essence, gross phase separation occurs between the silicone-based PSA and the acrylate-based PSA both in liquid form and upon drying. As is known in the art, phase separation is generally caused by the incompatibility of two dissimilar materials, such as in the simple example of oil and water. In this particular case, the lower surface energy of the silicone PSA becomes incompatible with the higher surface energy of the acrylate PSA and phase separation occurs. Phase separation is also commonly referred to as instability. This instability limits the effective use time of the acrylate pressure sensitive adhesive/silicone pressure sensitive adhesive blend prior to and during application before phase separation occurs. Also, upon drying and as the blend ages over time, the size of the domains can potentially change as the two distinct PSAs try to reach an equilibrium state. This can lead to changes in properties such as tack, skin adhesion, and release from liner with time.

In another example, JP 62-295982, to Toyoda Gosei Co. LTD, describes a mounting system for an automotive application that consists of a molding and a PSA made by combining a silicone-based PSA, an acrylate-based PSA, and a polyurethane and/or polyisocyanate crosslinker together. The purpose of this mounting system is to provide a composition to mount a molding to an automobile main frame. For the silicone-based PSA and the acrylate-based PSA to be put together, a third polymeric species, specifically the polyurethane and/or polyisocyanate crosslinker, must be used to react the separate phases together. The disadvantages of this system include the requirement for the third polymeric species, a limited formulated pot life due to immediate reaction of the crosslinker, and unstable shelf-life stability of the coated product as the system will continue to crosslink with age, i.e., over time.

U.S. Pat. No. 4,791,163 to General Electric Company describes an emulsion that comprises (a) 100 parts by weight of water; (b) 10 to 400 parts by weight of PSA comprising: (i) from about 50 to 99% by weight of an organic PSA; (ii) from 1 to about 50% by weight of a silicone PSA; and (c) an effective amount of emulsifying agent to maintain the emulsion. The silicone-based PSA in solvent is first emulsified and then subsequently added to the organic PSA to provide the final composition. In this example, it is necessary to have careful control of the emulsifying agent and drying conditions to prevent premature phase separation of the emulsion prior to and during the drying step. Once the emulsion has been dried, there is no actual chemical reaction that occurs between the silicone PSA and the organic PSA.

Another example, EP 0 289 929 B1 also to the General Electric Company, describes the same emulsion as in the '163 patent with the addition of an effective amount of organic peroxide or alkoxy silane crosslinking agent to increase the shear strength of the emulsion through crosslinking within the silicone phase. Again, the emulsion requires the careful control of the emulsifying agent to prevent gross phase separation of the emulsion prior to and during the drying step.

In another example, JP 63-291971, to Nitto Electric Ind. Co. LTD, describes an adhesive that comprises a mixture of a silicone PSA, an acrylate PSA, and a silicone-acrylic graft copolymer. The silicone-acrylic graft copolymer is formed by the reaction of a silicone macromonomer with acrylic monomers during a polymerization reaction. The silicone-acrylic graft copolymer is then added to a blend of silicone PSA and acrylic PSA composition to act as a compatibilizer between the two different PSA phases. Because there is no actual chemical reaction between the PSAs, there still remains the potential for phase separation.

In WO 92/20751 to Minnesota Mining and Manufacturing Company (3M), a pressure sensitive adhesive composition preferably consists of acrylic monomer, a silicone pressure-sensitive adhesive, optional photoinitiator and optional crosslinker. Another series of 3M patents relating to vibration damping disclose this same composition (see WO 92/20752, and U.S. Pat. Nos. 5,464,6659 and 5,624,763). The goal of these compositions is to provide a solventless, radiation curable composition for use in PSA or vibration damping applications. The commercially available silicone PSA is first dried of all solvent. The solid silicone PSA mass is then dissolved in the desired monomer(s) followed by the addition of the photoinitiator and the crosslinker. The composition is then coated onto a substrate and cured into a final product by exposure to UV radiation. Although a crosslinker can be added, the composition is essentially an interpenetrating network where the acrylic monomer reacts while dispersed within the preformed silicone PSA network. The advantages of this composition are the ability to control the silicone PSA to acrylate ratio and also the ratio of acrylate monomer(s) within the acrylate itself depending on final use properties. As is clearly stated throughout these patents, the components of the composition are selected such that when the silicone PSA has been dispersed into the monomers to form a homogeneous mixture, the components will not exhibit phase separation when left at room temperature over a period of 12 hours. This still is a disadvantage in the fact that the materials will eventually phase separate with time. Another distinct disadvantage is that this system is typically cured in a substantially oxygen-free atmosphere or a nitrogen atmosphere. Therefore, handling becomes more complicated and pot-life of the formulated material becomes limited. Lastly, the use of photoinitiators in the UV-curing composition and their potential by-products almost certainly precludes its use in applications such as transdermal drug delivery systems which are loaded with active agents that could react or degrade in such environments. As alluded to above, there remains a need to improve upon the pressure sensitive adhesives of the prior art.

SUMMARY OF THE INVENTION AND ADVANTAGES

A single phase silicone acrylate formulation that resists phase separation includes (A) at least one of a silicone, an acrylate, and combinations thereof. The formulation also includes (B) a silicone acrylate hybrid compatibilizing agent including silicone functionality and (meth)acrylate functionality and is the reaction product of a silicon-containing pressure sensitive adhesive composition, a (meth)acrylate monomer, and an initiator. A method of minimizing phase separation of the single phase silicone acrylate formulation includes the step of combining (A) and (B) to form the single phase silicone acrylate formulation. The silicone acrylate hybrid compatibilizing agent integrates the advantageous functionalities associated with both acrylate and silicone chemistries into the single phase silicone acrylate formulation that resists phase separation.

DETAILED DESCRIPTION

This invention provides a single phase silicone acrylate formulation (hereinafter referred to as the single phase formulation). The single phase formulation resists phase separation, is one phase, and is not bi-phasic or a two phase system. In other words, the single phase formulation is not phase separated. Most typically, the single phase formulation does not phase separate, as determined using visual evaluation, after resting for 1 hour, 24 hours, 3 to 7 days, 1 week, 2 weeks, 3 weeks, 4 weeks, or after 1 month, at about room temperature. It is contemplated that the single phase formulation may resist phase separation and not phase separate after resting for 2, 3, 4, 5, or 6 months, from 6 months to one year, after one year, or ever, at room temperature.

Typically, the single phase formulation is a homogenous or dispersed mixture or combination of (A) least one of a silicone, an acrylate, and combinations thereof and (B) a silicone acrylate hybrid compatibilizing agent (hereinafter referred to as the compatibilizing agent). In one embodiment, (A) is present in a greater weight or volume percent than (B). Alternatively, (B) may be present in a greater weight or volume percent than (A). In various embodiments, (A) is present in an amount of from about 10 to about 90, from about 20 to about 80, from about 30 to about 70, from about 40 to about 60, or about 50, weight percent of the total formation. In other embodiments, (B) is present in an amount of from about 10 to about 90, from about 20 to about 80, from about 30 to about 70, from about 40 to about 60, or about 50, weight percent of the total formation.

(A) is not particularly limited and may include any silicone or acrylate known in the art. Suitable non-limiting examples of the (A) silicone include polysiloxanes such as PDMS, silicones that include one or more M, D, T, and/or Q units, a (condensation) reaction product of a silanol endblocked PDMS and a silicate resin, trimethylsiloxy capped derivates thereof, and combinations thereof. In one embodiment, the (A) silicone is a pressure sensitive adhesive, as known in the art. The (A) acrylate is typically a polymer that is typically formed from the polymerization of one or more acrylate monomers. The acrylate monomers are not particularly limited and may be any known in the art such as acrylate, methacrylate, methylmethacrylate, and the like. In one embodiment, the (A) acrylate includes 2-ethylhexyl acrylate and methacrylate.

Additional non-limiting examples of suitable (A) silicones and acrylates include silicone pressure sensitive adhesive compositions, acrylic pressure sensitive adhesive compositions, and physical blends thereof. One such blend is a blend of acrylic and rubber pressure sensitive adhesive compositions. Even additional non-limiting examples are disclosed in U.S. Pat. Nos. 5,474,783; 5,656,286; 6,024,976; 6,221,383;

6,235,306; 6,465,004; 6,638,528; 5,464,659; and 5,624,763, the disclosures of which are hereby incorporated by reference in their entirety.

Referring back, the (B) compatibilizing agent comprises silicone functionality and (meth)acrylate functionality. The silicone and/or (meth)acrylate functionality may alternatively be described as silicone and/or (meth)acrylate content or as a silicone and/or (meth)acrylate polymeric or polymerized group of the (B) compatibilizing agent. The silicone functionality is typically represented in the compatibilizing agent as —Si—O—Si— bonds/groups which may be M, D, T, or Q units, as known in the art. It is to be understood that the compatibilizing agent can include acrylate functionality, methacrylate functionality, or both acrylate functionality and methacrylate functionality.

The (B) compatibilizing agent is (or includes) the reaction product of silicon-containing pressure sensitive adhesive composition, a (meth)acrylate monomer, and an initiator (i.e., in the presence of the initiator). That is, the (B) compatibilizing agent is the product of the chemical reaction between these reactants (the silicon-containing pressure sensitive adhesive composition, the (meth)acrylate monomer, and the initiator). The (B) compatibilizing agent of the present invention may also be referred to as a silicone acrylic compatibilizing agent as the terms acrylate and acrylic are generally used interchangeably throughout this description. As used in the description of the present invention, the terms silicone acrylate and silicone acrylic are intended to denote more than a simple blend of a silicone-based sub-species and an acrylate-based sub-species. Instead, these terms denote a polymerized hybrid species that includes silicone-based sub-species and acrylate-based sub-species that have been polymerized together.

The term 'pressure sensitive adhesive' and the acronym 'PSA' are used interchangeably throughout the subject description. As just one example, the silicon-containing pressure sensitive adhesive composition may also be referred to as the silicon-containing PSA composition. The silicon-containing pressure sensitive adhesive composition is typically reacted with the (meth)acrylate monomer to form the (B) compatibilizing agent in an amount of from 5 to 95, more typically 25 to 75, parts by weight based on 100 parts by weight of the (B) compatibilizing agent.

In one embodiment, the silicon-containing pressure sensitive adhesive composition itself comprises the condensation reaction product of a pressure sensitive adhesive and a silicon-containing capping agent. As also explained additionally below, the silicon-containing capping agent may provide acrylate or methacrylate functionality to the silicon-containing pressure sensitive adhesive. It is to be understood that, in the context of the description of the present invention, the term 'pressure sensitive adhesive' is distinguishable from the term 'silicon-containing pressure sensitive adhesive composition'.

The silicon-containing pressure sensitive adhesive composition, as described above, may be the reaction product of the pressure sensitive adhesive and a silicon-containing capping agent or the condensation reaction product of a silicone resin, a silicone polymer, and a first and/or a second silicon-containing capping agent. The silicon-containing pressure sensitive adhesive composition may be a pressure sensitive adhesive that has been capped or endblocked with the capping agent or agents described herein. The capping agent and the pressure sensitive adhesive may react to form the silicon-containing pressure sensitive adhesive composition.

In one embodiment, the pressure sensitive adhesive (before reaction with the capping agent) comprises the condensation reaction product of the silicone resin and the silicone polymer, which may optionally react in the presence of a catalyst, such as a condensation catalyst, e.g. an acid or base catalyst. Alternatively, the capping agent may provide an in-situ catalyst upon reaction, e.g. as HCl generated from chlorosilane. In this embodiment, an independent catalyst may be used or may be omitted. Typically, the silicone resin reacts in an amount of from 30 to 80 parts by weight to form the pressure sensitive adhesive, and the silicone polymer reacts in an amount of from 20 to 70 parts by weight to form the pressure sensitive adhesive. Both of these parts by weight are based on 100 parts by weight of the pressure sensitive adhesive. Although not required, the pressure sensitive adhesive may comprise a catalytic amount of a condensation catalyst.

There is a wide array of silicone resins and silicone polymers that are suitable. Suitable silicone resins and silicone polymers include, but are not limited to, those disclosed and described in U.S. Pat. No. 6,337,086 to Kanios et al., the disclosure of which is incorporated by reference herein in its entirety.

One silicone resin comprises a copolymer comprising triorganosiloxy units of the formula $R^3_3SiO_{1/2}$ and tetrafunctional siloxy units of the formula $SiO_{4/2}$ in a ratio of about 0.6 to 0.9 triorganosiloxy units for each tetrafunctional siloxy unit, wherein each $R^3$ independently denotes a monovalent hydrocarbon radical having from 1 to 6 carbon atoms, and a typical silicone polymer comprises at least one polydiorganosiloxane comprising $AR^3SiO$ units terminated with endblocking $TR^3ASiO1/2$ units, wherein the polydiorganosiloxane has a viscosity of from about 100 centipoise to about 30,000,000 centipoise at 25° C., each A radical is independently selected from $R^3$ or halohydro-carbon radicals having from 1 to 6 carbon atoms, each T radical is independently selected from the group consisting of $R^3$, OH, H or $OR^4$, and each $R^4$ is independently an alkyl radical having from 1 to 4 carbon atoms.

As an example using forms of this silicone resin and this silicone polymer, one type of pressure sensitive adhesive is made by:

mixing (i) from 30 to 80 inclusive parts by weight of at least one resin copolymer containing silicon-bonded hydroxyl radicals and consisting essentially of $R^3_3SiO_{1/2}$ units and $SiO_{4/2}$ units in a mole ratio of 0.6 to 0.9 $R^3_3SiO_{1/2}$ units for each $SiO_{4/2}$ unit present, (ii) between about 20 and about 70 parts by weight of at least one polydiorganosiloxane comprising $AR^3SiO$ units terminated with endblocking $TR^3ASiO1/2$ units, wherein the polydiorganosiloxane has a viscosity of from about 100 centipoise to about 30,000,000 centipoise at 25° C. and each $R^3$ is a monovalent organic radical selected from the group consisting of hydrocarbon radicals of from 1 to 6 inclusive carbon atoms, each A radical is independently selected from $R^3$ or halohydrocarbon radicals having from 1 to 6 inclusive carbon atoms, each T radical is independently selected from the group consisting of $R^3$, OH, H or $OR^4$, and each $R^4$ is independently an alkyl radical of from 1 to 4 inclusive carbon atoms; a sufficient amount of (iii) at least one of the silicon-containing capping agents, also referred to throughout as endblocking agents, described below and capable of providing a silanol content, or concentration, in the range of 5,000 to 15,000, more typically 8,000 to 13,000, ppm, when desirable an additional catalytic amount of (iv) a mild silanol condensation catalyst in the event that none is provided by (ii), and when necessary, an effective amount of (v) an organic solvent which is inert with respect to (i), (ii), (iii) and (iv) to reduce the viscosity of a mixture of (i), (ii), (iii), and (iv), and condensing the mixture of (i), (ii), (iii) and (iv) at least until a substantial amount of the silicon-containing capping agent or agents have reacted with the silicon-bonded hydroxyl radicals and T radicals of (i) and (ii). Additional organosilicon endblocking agents can be used in conjunction with the silicon-containing capping agent or agents (iii) of the present invention. Such additional organosilicon endblocking agents, also referred to herein as a second silicon-containing capping agent, are described additionally below.

The pressure sensitive adhesives are typically made in accordance with the present invention using from 30 to 80 inclusive parts by weight of silicone copolymer resins (i) and from 20 to 70 parts by weight of polydiorganosiloxane (ii) of the type which have been used in the past to make such adhesives. More typical are compositions employing from 40 to 75 parts by weight of resin copolymer (i) and from 25 to 60 parts by weight of polydiorganosiloxane (ii).

The silicone resin copolymers (i) contain silicon-bonded hydroxyl radicals in amounts which typically range from about 1 to 4 weight percent of silicon-bonded hydroxyl radicals and comprise triorganosiloxy units of the formula $R^3{}_3SiO_{1/2}$ and tetrafunctional siloxy units of the formula $SiO_{4/2}$ in a mole ratio of from 0.6 to 0.9 $R^3{}_3SiO_{1/2}$ units for each $SiO_{4/2}$ unit present. Blends of two or more such copolymers may also be used. There should be at least some and typically at least 0.5% silicon-bonded hydroxyl content to enable the polydiorganosiloxane component to copolymerize with the copolymer resin and/or to react with the endblocking agent being added to chemically treat the pressure sensitive adhesive. These resin copolymers are generally benzene-soluble resinous materials which are typically solids at room temperature and are prepared as, and usually, but not necessarily used as, a solution in an organic solvent. Typical organic solvents used to dissolve resin copolymer (i) include benzene, toluene, xylene, methylene chloride, perchloroethylene, naphtha mineral spirits and mixtures of these.

Resin copolymer (i) consists essentially of from 0.6 to 0.9 $R^3{}_3SiO_{1/2}$ units for every $SiO_{4/2}$ unit in the copolymer. There may also be a few mole percent of $R^3{}_2SiO$ units present in the copolymer provided that the presence of such units does not cause the ultimate product of this process to lose its ability to function as a PSA. Each $R^3$ denotes, independently, a monovalent hydrocarbon radical having from 1 to 6 inclusive carbon atoms such as methyl, ethyl, propyl, isopropyl, hexyl, hexenyl, cyclohexyl, vinyl, allyl, propenyl and phenyl. Typically, the $R^3{}_3SiO_{1/2}$ units are $Me_3SiO_{1/2}$ units and/or $Me_2R^1SiO_{1/2}$ units wherein is $R^1$ is a vinyl ("Vi") or phenyl ("Ph") radical. More typically, no more than 10 mole percent of the $R^3{}_3SiO_{1/2}$ units present in resin copolymer (i) are $Me_2R^2SiO_{1/2}$ units and the remaining units are $Me_3SiO_{1/2}$ units where each $R^2$ is a vinyl radical. Most typically, the $R^3{}_3SiO_{1/2}$ units are $Me_3SiO_{1/2}$ units.

The mole ratio of $R^3{}_3SiO_{1/2}$ and $SiO_{4/2}$ units can be determined simply from knowledge of the identity of the $R^3$ radicals in the $R^3{}_3SiO_{1/2}$ units and the percent carbon analysis of the resin copolymer. In the typical resin copolymer consisting of from 0.6 to 0.9 $Me_3SiO_{1/2}$ units for every $SiO_{4/2}$ unit, the carbon analysis has a value of from 19.8 to 24.4 percent by weight.

Resin copolymer (i) may be prepared according to Daudt et al., U.S. Pat. No. 2,676,182 (issued Apr. 20, 1954 and hereby incorporated by reference) whereby a silica hydrosol is treated at a low pH with a source of $R^3{}_3SiO_{1/2}$ units such as a hexaorganodisiloxane such as $Me_3SiOSiMe_3$, $ViMe_2SiOSiMe_2Vi$ or $MeViPhSiOSiPhViMe$ or triorganosilane such as $Me_3SiCl$, $Me_2ViSiCl$ or $MeViPhSiCl$. Such copolymer resins are typically made such that the copolymer resin contains about 1 to 4 weight percent of silicon-bonded hydroxyl radicals. Alternatively, a mixture of suitable hydrolyzable silanes free of $R^3$ radicals may be cohydrolyzed and condensed. In this alternative procedure, it is a typical practice to further treat the copolymer product with a suitable silylating agent, such as hexamethyldisilazane or divinyltetramethyldisilazane, to reduce the silicon-bonded hydroxyl content of the copolymer product to less that 1 percent by weight. This step would not be necessary, but could be used, in the process now being described. Typically, the resin copolymers employed contain from about 1 to 4 weight percent of silicon-bonded hydroxyl radicals.

Ingredient (ii) is one or more polydiorganosiloxanes comprising $AR^3SiO$ units terminated with endblocking $TR^3ASiO1/2$ units, each of which polydiorganosiloxanes has a viscosity of from 100 centipoise to 30,000,000 centipoise at 25° C. (100 millipascal-seconds to 30,000 pascal seconds (Pa·s) where 1 centipoise equals 1 millipascal second). As is well-known, viscosity is directly related to the average number of diorganosiloxane units present for a series of polydiorganosiloxanes of varying molecular weights which have the same endblocking units. Polydiorganosiloxanes having a viscosity of from about 100 to 100,000 centipoise at 25° C. range from fluids to somewhat viscous polymers. These polydiorganosiloxanes are typically prereacted with resin copolymer (i) prior to condensation in the presence of endblocking agent (iii) to improve the tack and adhesion properties of the resulting pressure sensitive adhesive as will be further described. Polydiorganosiloxanes having viscosities in excess of 100,000 centipoise can typically be subjected to the condensation/endblocking step without prereaction. Polydiorganosiloxanes having viscosities in excess of 1,000,000 centipoise are highly viscous products often referred to as gums and the viscosity is often expressed in terms of a Williams Plasticity value (polydimethylsiloxane gums of about 10,000,000 centipoise viscosity typically have a Williams Plasticity Value of about 50 mils (1.27 mm) or more at 25° C.).

The polydiorganosiloxanes of (ii) consist essentially of $AR^3SiO$ units where each $R^3$ is as defined above. Each A radical is selected from radicals such as $R^3$ or halohydrocarbon radicals of from 1 to 6 inclusive carbon atoms such a chloromethyl, chloropropyl, 1-chloro-2-methylpropyl, 3,3,3-trifluoropropyl and $F_3C(CH_2)_5$ radicals. Thus, the polydiorganosiloxane can contain $Me_2SiO$ units, $PhMeSiO$ units, $MeViSiO$ units, $Ph_2SiO$ units, methylethylsiloxy units, 3,3,3-trifluoropropyl units and 1-chloro, 2-methylpropyl units and the like. Typically, the $AR^3SiO$ units are selected from the group consisting of $R^3{}_2SiOR^3R^4SiO$ units, $Ph_2SiO$ units and combinations of both where $R^3$ and $R^4$ are as above, at least 50 mole percent of the $R^4$ radicals present in the polydiorganosiloxane (ii) are methyl radicals and no more than 50 mole percent of the total moles of $AR^3SiO$ units present in each polydiorganosiloxane of (ii) are $Ph_2SiO$ units. More typically, no more than 10 mole percent of the $AR^3SiO$ units present in each polydiorganosiloxane (ii) are $MeR^3SiO$ units where $R^3$ is as above defined and the remaining $AR^3SiO$ units present in each polydiorganosiloxane are $Me_2SiO$ units. Most typically, substantially all of the $AR^3SiO$ units are $Me_2SiO$ units.

Each polydiorganosiloxane (ii) is terminated with endblocking units of the unit formula $TR^3ASiO_{1/2}$ where $R^3$ and A are as defined above and each T radical is $R^3$, OH, H or $OR^4$ radicals where each $R^4$ is an alkyl radical of from 1 to 4 inclusive carbon atoms such as methyl, ethyl, n-propyl, and isobutyl radicals. H, OH and $OR^4$ provide a site for reaction with the acrylate or methacrylate functional silicon-containing capping agent and also provide a site for condensation with other such radicals on polydiorganosiloxanes (ii) or with the silicon-bonded hydroxyl groups present in resin copolymer (i). Use of polydiorganosiloxanes where T is OH is most typical because the polydiorganosiloxane (ii) can then readily copolymerize with the resin copolymer (i). When an appropriate catalyst such as HCl, which is generated when chlorosilanes are used, or ammonia, which is generated when organosilazanes are used as endblocking agents, then triorganosiloxy (e.g., $R^3{}_3SiO_{1/2}$ such as $(CH_3)_3SiO_{1/2}$ or $CH_2CH(CH_3)_2SiO_{1/2}$) unit terminated polydiorganosiloxanes can be employed because some of the triorganosiloxy units can be cleaved when the condensation reaction is conducted with heating. The cleavage exposes a silicon-bonded hydroxyl radical which can then condense with silicon-bonded hydroxyl radicals in the copolymer resin, with endblocking triorganosilyl units or with other polydiorganosiloxanes containing H, OH or $OR^4$ radicals or silicon-bonded hydroxyl radicals exposed by cleavage reactions. Mixtures of polydiorganosiloxanes containing different substituent radicals may also be used.

Methods for the manufacture of such polydiorganosiloxanes are well known as exemplified by the following U.S. Pat. Nos. 2,490,357 (Hyde); 2,542,334 (Hyde); 2,927,907 (Polmanteer); 3,002,951 (Johannson); 3,161,614 (Brown, et al.); 3,186,967 (Nitzche, et al.); 3,509,191 (Atwell), and 3,697,473 (Polmanteer, et al.) which are hereby incorporated by reference.

To obtain pressure sensitive adhesives which are to be cured by peroxide or through aliphatically unsaturated radicals present in resin copolymer (i) or polydiorganosiloxane (ii), if resin copolymer (i) contains aliphatically unsaturated radicals, then polydiorganosiloxane (ii) should be free of such radicals and vice-versa. If both components contain aliphatically unsaturated radicals, curing through such radicals can result in products which do not act as pressure sensitive adhesives.

As alluded to above, the pressure sensitive adhesive may include a concentration of silicon bonded hydroxyl groups (i.e., silanols) and the silicon-containing capping agent is an endblocking agent. Once again, the terms endblocking agents and capping agents are used interchangeably throughout the art and in the subject description. The endblocking agent and the pressure sensitive adhesive may be condensed to produce the silicon-containing pressure sensitive adhesive composition. More specifically, the endblocking agent may react with the concentration of silicon bonded hydroxyl groups to cap the pressure sensitive adhesive. As generally alluded to above, if the endblocking agent reacts with the pressure sensitive adhesive, the concentration of silanols in the composition is from 5,000 to 15,000, more typically from 8,000 to 13,000, ppm.

Although not required, the pressure sensitive adhesive is typically present in the silicon-containing pressure sensitive adhesive composition in an amount of from 85.0 to 99.9 parts by weight based on weight % solids of the pressure sensitive adhesive, and the silicon-containing capping agent is typically present in the silicon-containing pressure sensitive adhesive composition in an amount of from 0.1 to 15 parts by weight based on weight % solids of the pressure sensitive adhesive. More typically, the pressure sensitive adhesive is present in the silicon-containing pressure sensitive adhesive composition in an amount of from 90.0 to 99.8 parts by weight based on weight % solids of the pressure sensitive adhesive, and the silicon-containing capping agent is typically present in the silicon-containing pressure sensitive adhesive composition in an amount of from 0.2 to 10 parts by weight based on weight % solids of the pressure sensitive adhesive. Typically, the pressure sensitive adhesive has a weight % solids of from 50 to 65%, more typically 60%.

The endblocking agent can be introduced to react with the pressure sensitive adhesive after the pressure sensitive adhesive has already been formed, i.e., after the silicone resin and the silicone polymer which make up the pressure sensitive adhesive have reacted. In this case, the silicon-containing capping agent reacts with the pressure sensitive adhesive after the silicone resin and the silicone polymer have been condensation reacted to form the pressure sensitive adhesive.

Alternatively, the endblocking agent can be reacted in situ with the silicone resin and/or the silicone polymer such that the endblocking agent is present as the silicone resin and the silicone polymer are reacting. That is, in this in situ scenario, the endblocking agent may be introduced either prior to or during the reaction of the silicone resin and the silicone polymer. In any event, in this in situ scenario, the silicone resin and the silicone polymer are reacted in the presence of the silicon-containing capping agent, and the silicon-containing capping agent is reacted in situ with the silicone resin and the silicone polymer as the silicone resin and the silicone polymer are condensation reacting to form the pressure sensitive adhesive.

In one embodiment of the present invention, the silicon-containing capping agent is selected from the group of acrylate functional silanes, acrylate functional silazanes, acrylate functional disilazanes, acrylate functional disiloxanes, methacrylate functional silanes, methacrylate functional silazanes, methacrylate functional disilazanes, methacrylate functional disiloxanes, and combinations thereof.

Alternatively, the endblocking agent may be described to be of the general formula $(XYR_2Si)_2D$ wherein X is a monovalent radical of the general formula AE- where E is —O— or —NH— and A is an acryl group or a methacryl group, Y is a divalent alkylene radical having from 1 to 6 carbon atoms, R is a methyl or a phenyl radical, and D is a divalent or a trivalent organic hydrolyzable radical. Typically, D is —O— or —NH—. Most typically, this particular endblocking agent is selected from the group of Bis(3-methacryloxypropyl)tetramethyldisilazane, Bis(3-acryloxypropyl)tetramethyl disilazane, Bis(3-methacryloxypropyl) tetramethyldisiloxane, Bis(3-acryloxypropyl) tetramethyldisiloxane, and combinations thereof.

The acryl group provides the silicon-containing capping agent with acrylate functionality and the methacryl group provides the silicon-containing capping agent with the methacrylate functionality. Those skilled in the art recognize that the acryl group can be generically represented as

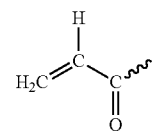

The methacryl group can be generally represented as

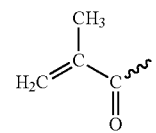

Even further, the endblocking agent may be described to be of the general formula $XYR'_bSiZ_{3-b}$ wherein X is a monovalent radical of the general formula AE- where E is —O— or —NH— and A is an acryl group or a methacryl group as set forth above, Y is a divalent alkylene radical having from 1 to 6 carbon atoms, R' is a methyl or a phenyl radical, Z is a monovalent hydrolyzable organic radical or a halogen, and b is 0, 1, or 2. Typically, the monovalent hydrolyzable organic radical is of the general formula R"O— where R" is an alkylene radical. Most typically, this particular endblocking agent is selected from the group of 3-methacryloxypropyldimethylchlorosilane, 3-methacryloxypropyldichlorosilane, 3-methacryloxypropyltrichlorosilane, 3-methacryloxypropyldimethylmethoxysilane, 3-methacryloxypropylmethyldimethoxysilane, 3-methacryloxypropyltrimethoxysilane, 3-methacryloxypropyldimethylethoxysilane, 3-methacryloxypropylmethyldiethoxysilane, 3-methacryloxypropyltriethoxysilane, (methacryloxymethyl)dimethylmethoxysilane, (methacryloxymethyl)methyldimethoxysilane, (methacryloxymethyl)trimethoxysilane, (methacryloxymethyl)dimethylethoxysilane, (methacryloxymethyl)methyldiethoxysilane, methacryloxymethyltriethoxysilane, methacryloxypropyltriisopropoxysilane, 3-methacryloxypropyldimethylsilazane, 3-acryloxypropyldimethylchlorosilane, 3-acryloxypropyldichlorosilane, 3-acryloxypropyltrichlorosilane, 3-acryloxypropyldimethylmethoxysilane, 3-acryloxypropylmethyldimethoxysilane, 3-acryloxypropyltrimethoxysilane, 3-acryloxypropyldimethylsilazane, and combinations thereof.

As alluded to above, a second silicon-containing capping agent can be used in conjunction with the silicon-containing capping, or endblocking, agent of the present invention. This second silicon-containing capping agent is distinguishable from the silicon-containing capping agent in that the second silicon-containing capping agent is typically free of acrylate and methacrylate functionality. If included, the second silicon-containing capping agent, an organosilicon endblocking agent, is along with the silicon-containing capping agent and the pressure sensitive adhesive a reaction product that forms the composition. The second silicon-containing capping agent is typically capable of generating an endblocking triorganosilyl unit. Suitable second silicon-containing capping agents include, but are not limited to, those described in U.S. Pat. No. 6,337,086 to Kanios et al., the disclosure of which has already been incorporated by reference in its entirety.

Referring back, the (meth)acrylate monomer is a reactant that, along with the silicon-containing pressure sensitive adhesive and the initiator, reacts to form the (B) compatibilizing agent. Typically, the (meth)acrylate monomer and the silicon-containing pressure sensitive adhesive composition are polymerized in the presence of the initiator. The (meth) acrylate monomer is typically reacted to form the (B) compatibilizing agent in an amount of from 5 to 95, more typically from 25 to 75, parts by weight based on 100 parts by weight of the (B) compatibilizing agent. Although the present invention is described primarily in the context of one (meth)acrylate monomer, it is to be understood that more than one (meth)acrylate monomer, i.e., a combination of (meth)acrylate monomers, may be polymerized, more specifically copolymerized, along with the silicon-containing pressure sensitive adhesive and the initiator. Generally, the acrylic portion of the subject (B) compatibilizing agent, formed via the reaction of the (meth)acrylate monomer and the silicon-containing pressure sensitive adhesive, is typically formed similar to acrylate-based PSAs with a combination of monomers that can be broadly described as a main monomer and a modifying monomer as is described extensively in Chapter 19 of the Handbook of Pressure Sensitive Adhesive Technology, Third Edition, Donatas Satas, Satas & Associates, 1999, Warwick, R.I.

The (meth)acrylate monomer can be any monomer having at least one acrylate functional group and/or at least one methacrylate functional group. In other words, the terminology "(meth)" describes that the "meth" group is optional and not required. Thus, the monomer may be an acrylate monomer or a methacrylate monomer. It is typical that the (meth)acrylate monomer used in the present invention is a compound selected from the group of aliphatic acrylates, aliphatic methacrylates, cycloaliphatic acrylates, cycloaliphatic methacrylates, and combinations thereof. It is to be understood that each of the compounds, the aliphatic acrylates, the aliphatic methacrylates, the cycloaliphatic acrylates, and the cycloaliphatic methacrylates, include an alkyl radical. The alkyl radicals of these compounds can include up to 20 carbon atoms.

The aliphatic acrylates that may be selected as one of the (meth)acrylate monomers are selected from the group consisting of methyl acrylate, ethyl acrylate, propyl acrylate, n-butyl acrylate, iso-butyl acrylate, tert-butyl acrylate, hexyl acrylate, 2-ethylhexyl acrylate, iso-octyl acrylate, iso-nonyl acrylate, iso-pentyl acrylate, tridecyl acrylate, stearyl acrylate, lauryl acrylate, and mixtures thereof. The aliphatic methacrylates that may be selected as one of the (meth)acrylate monomers are selected from the group consisting of methyl methacrylate, ethyl methacrylate, propyl methacrylate, n-butyl methacrylate, iso-butyl methacrylate, tert-butyl methacrylate, hexyl methacrylate, 2-ethylhexyl methacrylate, iso-octyl methacrylate, iso-nonyl methacrylate, iso-pentyl methacrylate, tridecyl methacrylate, stearyl methacrylate, lauryl methacrylate, and mixtures thereof. The cycloaliphatic acrylate that may be selected as one of the (meth)acrylate monomers is cyclohexyl acrylate, and the cycloaliphatic methacrylate that may be selected as one of the (meth)acrylate monomers is cyclohexyl methacrylate.

Certain other monomers, described herein as polar monomers, may be used as the (meth)acrylate monomer and may include supplemental functionality such as hydroxyl functionality. A polar monomer as used herein is an acrylic or methacrylic monomer having at least one polar group such as hydroxyl, alkoxy, amino, and alkenyl heterocycles. Examples of these polar monomers that are useful in the present invention include, but are not limited to, hydrophilic (meth)acrylate monomers of an amphoteric, anionic, cationic or anionic nature which are polymerizable by radical polymerization. More specific examples of these polar monomers include, but are not limited to, acrylic acid, methacrylic acid, hydroxy ethyl acrylate, hydroxy ethyl methacrylate, hydroxy propyl acrylate, hydroxy propyl methacrylate, methoxyethyl acrylate, methoxyethyl methacrylate, aminoethyl acrylate, aminoethyl methacrylate, 2-N,N,N-trimethylammonium ethyl acrylate, 2-N,N,N-trimethylammonium ethyl methacrylate, or salts thereof and the like.

The (meth)acrylate monomer and the silicon-containing pressure sensitive adhesive composition are typically polymerized in the presence of the initiator. It is generally typical that the polymerization of the (meth)acrylate monomer and the silicon-containing pressure sensitive adhesive composition in the presence of the initiator is conducted at a temperature of from 50 to 100° C., more typically of from 65 to 90° C. It is to be understood that the method of the present invention can be employed in a batch process, semi-continuous process, or continuous process. The method of the present invention is also 'flexible' in that the method accounts for rate controlled addition of the (meth)acrylate monomer or monomers which also contributes to the ability to control the silicone to acrylic ratio as described below.

Although not required, the silicon-containing pressure sensitive adhesive composition, the (meth)acrylate monomer, and the initiator may be mixed to form a pre-reaction mixture prior to the step of polymerizing and this pre-reaction mixture may be combined with a solvent prior to the step of polymerization. If these optional steps are conducted, then the polymerization obviously occurs with the components in the pre-reaction mixture after the pre-reaction mixture has been combined with the solvent.

It is to be understood that there are many different initiation mechanisms contemplated for use in the present invention to initiate the polymerization of the silicon-containing pressure sensitive adhesive composition and the (meth)acrylate monomer. However, the typical initiator is that known throughout the art as a free radical initiator and is detailed in Chapter 3 of Principles of Polymerization, Fourth Edition, George Odian, Wiley-Interscience, 2004, New Jersey. Generally, free radical initiators include peroxides, azo compounds, redox initiators, and photo-initiators. The most typical free radical initiators for application in the present invention are selected from the group of peroxides, azo compounds, and combinations thereof. The initiator is typically present in the (B) compatibilizing agent in an amount of from 0.005 to 3, more typically from 0.01 to 2, parts by weight based on 100 parts by weight of the (B) compatibilizing agent. Notably, once the (B) compatibilizing agent is formed, peroxides can serve additional functions in the context of the present invention not relating to initiation. Specifically, peroxides can function has cross-linking agents as described additionally below.

For descriptive purposes only, a generic representation is included below to generally illustrate the polymerization of the silicon-containing pressure sensitive and the (meth)acrylate monomer in the presence of the initiator to make the inventive (B) compatibilizing agent.

During the polymerization of the (meth)acrylate monomer and the silicon-containing pressure sensitive adhesive, the silicone to acrylic ratio can be sufficiently controlled and optimized as desired. Controlling the silicone to acrylic ratio is desirable because the (B) compatibilizing agent can be optimized dependent on the end application for the (B) compatibilizing agent. The silicone to acrylic ratio can be controlled by a wide variety of mechanisms in and during the method. An illustrative example of one such mechanism is the rate controlled addition of the (meth)acrylate monomer or monomers to the silicon-containing pressure sensitive adhesive composition. In certain applications, it may be desirable to have the silicone-based sub-species, or the overall silicone content, to exceed the acrylate-based sub-species, or the overall acrylic content. In other applications, it may be desirable for the opposite to be true. Independent of the end application, the silicon-containing pressure sensitive adhesive composition is typically present in the (B) compatibilizing agent in an amount of from 5 to 95, more typically from 25 to 75, parts by weight based on 100 parts by weight of the (B) compatibilizing agent.

Typically, a solvent is used during the polymerization to make the (B) compatibilizing agent to decrease the viscosity of the reaction mixture which allows for adequate mixing and heat transfer. The solvent may be any suitable material which is inert to the reaction ingredients and does not interfere with the reaction itself. Suitable solvents include, but are not limited to, aliphatic hydrocarbons such as hexane and heptane; alcohols such as methanol, ethanol and butanol; ketones such as acetone, methyl ethyl ketone and methyl isobutyl ketone; esters such as ethyl acetate, n-butyl acetate and i-butyl acetate; low viscosity silicone oils with linear, cyclic or branched structures which have a boiling point below 250° C. and a viscosity below 100 centistokes such as octamethylcyclotetrasiloxane, decamethylcyclopentasiloxane and hexamethyldisiloxane; and mixtures of two or more of the above mentioned solvents. If utilized, the amount of solvent is typi-

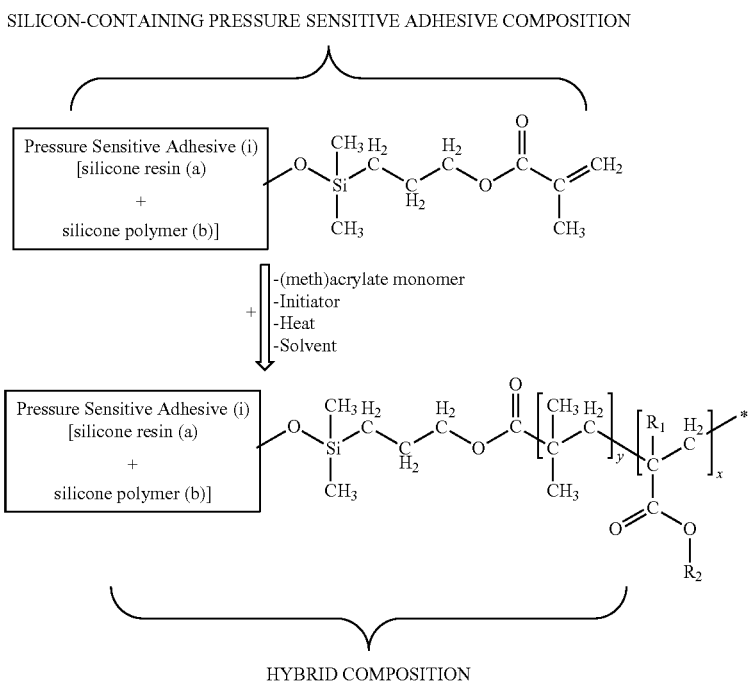

cally present in an amount of from 30 to 95, more typically 40 to 70, parts by weight based on the total amount of the reactants and solvent.

For cases where the molecular weight of the polymerization is to be controlled or limited, a chain transfer agent may be used. Chain transfer agents are known in the art and can include mercaptans, such as 1-butanethiol and dodecanethiol. If utilized, the amount of the chain transfer agent is typically from about 0 to 0.5 parts by weight per 100 parts by weight of the (B) compatibilizing agent.

The (B) compatibilizing agents described herein can be used as prepared to prepare PSA films for use as tapes or transdermal drug delivery systems in accordance with well-known coating, or application, techniques. Optionally, when an application requires higher shear strength (i.e., cohesive strength) than is afforded by the neat (B) compatibilizing agent, the crosslink density of the film resulting from the (B) compatibilizing agent can be increased in accordance with well-known procedures for both pure acrylate-based PSAs and pure silicone-based PSAs, which are described in Chapters 19 and 21, respectively, of the Handbook of Pressure Sensitive Adhesive Technology, Third Edition, Donatas Satas, Satas & Associates, 1999, Warwick, R.I.

When using the crosslinking techniques known for traditional acrylate PSAs for the (B) compatibilizing agents of the present invention, it is important to ensure that an amount of hydroxy or carboxylic functional monomer is incorporated into the initial polymerization steps for the (B) compatibilizing agent. The amount of this functional monomer should be present from 0.5 to 20 parts by weight based on total amount of monomer. If, for example, functional groups resulting from the incorporation of these functional monomers are available in the (B) compatibilizing agent, then the crosslink density is when various metal acetyl acetonates and orthoalkyl titanates are added prior to casting, i.e., coating. As is understood in the art, crosslink density is an indicator of static shear and cohesive strength. Such metal acetyl acetonates and orthoalkyl titanates are often referred to in the art as cross-linking agents. One specific suitable example of such a cross-linking agent is aluminum acetyl acetonate (AlAcAc). AlAcAc is used below in Example 29.

If the technique for curing, i.e., cross-linking, traditional silicone PSAs is used for the (B) compatibilizing agents of the present invention to improve static shear, then about 0.25 to 3.0% by weight of a peroxide cross-linking agent, such as dibenzoyl peroxide (BPO) or 2,4-dichlorobenzoylperoxide, based on the non-volatile content of the (B) compatibilizing agent, can be added to the (B) compatibilizing agent prior to casting. Once casted, the film can be cured at 110° C. to 175° C. for 1 to 10 minutes. As is known in the art, the peroxide cross-linking agent effectively extracts hydrogen off of one chain of the (B) compatibilizing agent and another hydrogen off of another chain of the (B) compatibilizing agent, and these two chains will then chemically react. One specific suitable example of a peroxide cross-linking agent is BPO. BPO is used below in Example 30.

In many of the applications described in the present invention, including tapes, labels and transdermal drug delivery systems, it is often necessary to use a backing layer and a release layer. The backing layer can be any of the typical substrates used for tapes such as those selected from polymeric films (e.g. polyethylene, polyester, polyimide, polyolefins, polypropylene, polyurethane, PTFE, etc.), metal foils, glass cloth, PTFE-coated glass cloth, paper (e.g. crepe, super-calendared craft, etc.), cloth, nonwoven materials, foams (e.g. polyurethane, acrylate, silicone, neoprene, etc.) and rubbers (e.g. silicone, butyl, etc.). Release liners are generally supplied on a backing such as paper or film and are applied to the (B) compatibilizing agent after the drying and/or curing steps are complete. Three general types of release coatings the are suitable for use with both silicone-based PSAs and acrylate-based PSAs, and also with the (B) compatibilizing agent of the present invention are known in the art and are commercially available: silicone-based release liners (e.g. Dow Corning® Syl-off™ 7680), perfluoropolyether-based release liners (e.g. 3M SCOTCH-PAK® 1022 Release Liner) and fluorosilicone-based release liners (e.g. Dow Corning® Syl-off™ Q2-7785). The release liner for a particular application will be dependant upon the ratio of silicone-to-acrylate in the (B) compatibilizing agent. For a (B) compatibilizing agent that contains a low level of silicon-containing PSA as compared to the (meth)acrylate monomer (e.g. 20 parts silicon-containing PSA and 80 parts (meth)acrylate monomer), a silicone-based release liner can be used. If the (B) compatibilizing agent contains a high level of silicone-containing PSA as compared to the (meth)acrylate monomer (e.g. 80 parts silicon-containing PSA and 20 parts (meth)acrylate monomer), then either a perfluoropolyether-based or fluorosilicone-based liner should be chosen.

One particularly important application for the (B) compatibilizing agent of the present invention is in a transdermal or a topical drug delivery system. The system includes an active agent and the (B) compatibilizing agent of the present invention functioning as a pressure sensitive adhesive. The active agent and its relationship to the (B) compatibilizing agent in the context of the system are described in detail below. As those skilled in the art appreciate, the system is structural and can be in many forms including, but not limited to, patches, films, multi-layer dressings, reservoir systems, and combinations thereof. The active agent is in the system for controlled transdermal delivery to a substrate. It is also possible, but not required, for the system to include a backing layer for supporting the (B) compatibilizing agent, and/or a release liner for protecting the (B) compatibilizing agent and/or the active agent prior to the controlled transdermal delivery of the active agent to the substrate. One typical application of the transdermal drug delivery system of the present invention is to treat a user, or patient, with the active agent. As a result, the substrate is typically the skin of the user and, in this typical application, the user applies and wears the system on their skin.

The active agent can be any component suitable for transdermal delivery to a substrate. Suitable active agents include, but are not limited to, those active agents disclosed and described in U.S. Pat. No. 5,474,783 to Miranda et al., the disclosure of which is incorporated by reference herein in its entirety. These active agents include, but are not limited to, cardioactive medications, androgenic steroids, estrogens, hormones, progestational agents, drugs having an action on the central nervous system, nutritional agents, anti-inflammatory agents, antihistamines, respiratory agents, sympathomimetics, miotics, cholinergic agonists, antimuscarinic or muscarinic cholinergic blocking agents, mydriatics, psychicenergizers, anti-infectives, dermatological agents, humoral agents, antispasmodics, antidepressant drugs, anti-diabetic, anorectic drugs, anti-allergenics, tranquilizers, antipsychotics, decongestants, antipyretics, antimigrane agents, drugs for treating nausea and vomiting, anti-malarials, anti-ulcerative agents, peptides, drugs for Parkinson's disease, drugs for spasticity, drugs for acute muscle spasms, anti-estrogen, anti-hormone agents, therapeutic agents, and combinations thereof.

More specific examples of the active agents outlined above that are suitable for implementation as the active agent in the present invention include:

Cardioactive medications, illustratively, organic nitrates such as nitroglycerin, isosorbide dinitrate and, isosorbide mononitrates; quinidine sulfate; procainamide; thiazides such as bendroflumethiazide, chlorothiazide, and hydrochlorothyazide; nifedipine; nicardipine; adrenergic blocking agents, such as timolol, and propranolol; verapamil; diltiazem; captopril; clonidine and prazosin;

Androgenic steroids, such as testosterone, methyltestosterone and fluoxymesterone;

Estrogens, such as, conjugated estrogens, esterified estrogens, quinestrol, estropipate, 17-β estradiol, 17-β estradiol valerate, equilin, mestranol, estrone, estriol, 17-β ethinyl estradiol, and diethylstilbestrol;

Progestational agents, such as progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17-alpha-hydroxyprogesterone, dydrogesterone, dimethisterone, ethinylestrenol, norgestrel, demegestone, promegestone, and megestrol acetate;

Drugs having an action on the central nervous system, for example sedatives, hyponotics, antianxiety agents, analgesics and anesthetics, such as chloral, buprenorphine, naloxone, haloperidol, fluphenazine, pentobarbital, phenobarbital, secobarbital, codeine, lidocaine, tetracaine, dyclonine, dibucaine, cocaine, procaine, mepivacaine, bupivacaine, etidocaine, prilocalne, benzocaine, fentanyl, and nicotine;

Nutritional agents, such as vitamins (e.g. niacinamide), essential amino acids and essential fats;

Anti-inflammatory agents, such as hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, ibuprofen, naproxen, fenoprofen, fenbufen, flurbiprofen, acetaminophen, indoprofen, ketoprofen, suprofen, indomethacin, piroxicam, aspirin, salicylic acid, diflunisal, methyl salicylate, phenylbutazone, sulindac, mefenamic acid, meclofenamate sodium, naproxen, and the like;

External analgesics, such as camphor, menthol, capsicum extract, frankincense, green tea, juniper tea, and caffeine;

Antihistamines, such as diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, terrenadine, and chlorpheniramine;

Respiratory agents, such as theophylline and Beta-adrenergic agonists such as albuterol, terbutaline, metaproterenol, ritodrine, carbuterol, fenoterol, quinterenol, rimiterol, solmefamol, soterenol, and tretoquinol;

Sympathomimetics such as dopamine, norepinephrine, phenylpropanolamine, phenylephrine, pseudoephedrine, amphetamine, propylhexedrine and epinephrine;

Miotics such as pilocarpine, and the like;

Cholinergic agonists, such as choline, acetylcholine, methacholine, carbachol, bethanechol, pilocarpine, muscarine, and arecoline;

Antimuscarinic or muscarinic cholinergic blocking agents, such as atropine, scopolamine, homatropine, methscopolamine, homatropine methylbromide, methantheline, cyclopentolate, tropicamide, propantheline, anisotropine, dicyclomine, and eucatropine;

Mydriatics, such as atropine, cyclopentolate, homatropine, scopolamine, tropicamide, eucatropine and hydroxyamphetamine;

Psychicenergizers, such as 3-(2-aminopropy)indole, 3-(2-aminobutyl)indole, and the like;

Anti-infectives, such as antibiotics, including penicillin, tetracycline, chloramphenicol, sulfacetamide, sulfadiazine, sulfamethoxazole and sulfisoxazole; antivirals, including idoxuridine; antibacterials, such as erythromycin and clarithromycin; anti-fungals, such as ketoconazole, and other anti-infectives including nitrofurazone, cyclopirox, terbafine, witch hazel, and the like;

Dermatological agents, such as retinoids; vitamins C and E; benzoyl peroxide (BPO) (also commonly referred to as dibenzoyl peroxide) and dapsone;

Humoral agents, such as the prostaglandins, natural and synthetic, for example PGE1, PGE 2-alpha, and PGF 2-alpha, and the PGE1 analog misoprostol;

Antispasmodics, such as atropine, methantheline, papaverine, cinnamedrine, and methscopolamine;

Antidepressant drugs, such as paroxetine, phenelzine, tranylcypromine, imipramine, amitriptyline, trimipramine, doxepin, desipramine, nortriptyline, protriptyline, amoxapine, maprotiline, and trazodone;

Anti-diabetics, such as insulin, and anticancer drugs such as tamoxifen and methotrexate;

Anorectic drugs, such as, dextroamphetamine, methamphetamine, phenylpropanolamine, fenfluramine, diethylpropion, mazindol, and phentermine.

Anti-allergenics, such as antazoline, methapyrilene, chlorpheniramine, pyrilamine and pheniramine;

Tranquilizers, such as reserpine, chlorpromazine, and antianxiety benzodiazepines such as alprazolam, chlordiazepoxide, clorazeptate, halazepam, oxazepam, prazepam, clonazepam, flurazepam, triazolam, lorazepam and diazepam;

Antipsychotics, such as thiopropazate, chlorpromazine, triflupromazine, mesoridazine, piperacetazine, thioridazine, acetophenazine, fluphenazine, perphenazine, trifluoperazine, chlorprothixene, thiothixene, haloperidol, bromperidol, loxapine, and molindone;

Decongestants, such as phenylephrine, ephedrine, naphazoline, tetrahydrozoline;

Antipyretics, such as aspirin, salicylamide, and the like;

Antimigrane agents, such as dihydroergotamine and pizotyline;

Drugs for treating nausea and vomiting, such as chlorpromazine, perphenazine, prochlorperazine, promethazine, triethylperazine, triflupromazine, and trimeprazine;

Anti-malarials, such as the 4-aminoquinolines, alphaminoquinolines, chloroquine, and pyrimethamine;

Anti-ulcerative agents, such as misoprostol, omeprazole, and enprostil;

Peptides, such as growth releasing factor;

Drugs for Parkinson's disease, spasticity, and acute muscle spasms such as levodopa, carbidopa, amantadine, apomorphine, bromocriptine, selegiline (deprenyl), trihexyphenidyl hydrochloride, benztropine mesylate, procyclidine hydrochloride, baclofen, diazepam, and dantrolene; and Anti-estrogen or hormone agents, such as tamoxifen or human chorionic gonadotropin.

In one embodiment, the active agent is selected from the group of ketoprofen, estradiol, clonidine, and combinations thereof.

As indicated above, the particular active agent is not limited to those recited above. Other examples of suitable active agents for use in the systems will be apparent to those skilled in the art (See, for example, pages 149-217 of Yie Chien's treatise entitled "Novel Drug Delivery Systems" which is Volume 14 of Drugs and the Pharmaceutical Sciences, Marcel Dekker, Inc., New York, N.Y. 10016 (1982)).

As those skilled in the art appreciate, the active agents can be present in the system in different forms, depending on which form yields optimum delivery characteristic, such as the release rate and the total amount released as described below. For example, in the case of drugs, the drug can be in its free base or acid form, or in the form of salts, esters, or any other pharmacologically acceptable derivatives, or even as components of molecular complexes.

The amount of the active agent incorporated into the system varies depending on many factors including, but not limited to, the particular active agent, the desired therapeutic effect, and the time span for which the system is to provide therapy. For most active agents, the passage of the active agent through the skin is the rate-limiting step in transdermal delivery. Thus, the amount of the active agent and the rate of release are typically selected so as to provide transdermal delivery characterized by a zero order time dependency for a prolonged period of time. The minimum amount of active agent in the system is selected based on the amount of active agent which passes through the skin, or other substrate, in the time span for which the system is to provide therapy. Typically, the amount of active agent in the system varies from about 0.1% up to about 60% by weight of the system, more typically from about 0.3% up to about 50% by weight of the system, and for the lower drug doses permitted by this invention, most typically from about 1.0% up to about 30% by weight of the system. The weight of the system is, at a minimum, the combined weight of the active agent and the (B) compatibilizing agent. Specific examples of these weight % ranges for the amount of active agent in the system are provided immediately below in the context of three typical active agents, specifically 17-β estradiol, niacinamide, and ketoconazole.

When the active agent comprises 17-β estradiol, the 17-β estradiol is typically present in an amount of 1.5 to 2.5, 4 to 6, or 7 to 13, parts by weight based on 100 parts by weight of the system depending on the particular drug dosage desired. 2, 5, or 10 parts by weight on this same basis are more typical values for the 17-β estradiol as the active agent.

When the active agent comprises niacinamide, the niacinamide is typically present in an amount of 1.5 to 2.5, 4 to 6, or 7 to 13, parts by weight based on 100 parts by weight of the system depending on the particular drug dosage desired. 2, 5, or 10 parts by weight on this same basis are more typical values for the niacinamide as the active agent.

When the active agent comprises ketoconazole, the ketoconazole is typically present in an amount of 1.5 to 2.5, 4 to 6, or 7 to 13, parts by weight based on 100 parts by weight of the system depending on the particular drug dosage desired. 2, 5, or 10 parts by weight on this same basis are more typical values for the ketoconazole as the active agent.

The aforementioned weight percentages are not limiting and the weight percentage of any one or more active agents may be selected by one of skill in the art. Additional typical, but non-limiting weight percentages of various active agents, are from about 0.1 to about 20, from about 1 to about 10, from about 2 to about 8, from about 3 to about 9, from about 4 to about 6, or about 5, parts by weight per 100 parts by weight of the formulation.

Furthermore, relative to the active agent, it is to be recognized that the active agent is most typically disposed in the (B) compatibilizing agent. However, it is also to be understood that the active agent and the (B) compatibilizing agent may coexist in the system in discrete layers. That is, in certain embodiments, the active agent is not disposed, or directly incorporated, into the (B) compatibilizing agent.

Of course, the transdermal drug delivery system can also contain other agents known to accelerate the delivery of the active agent through the skin or other substrate. These other agents are also referred to in the art as skin-penetration or permeation enhancers, excipients, accelerants, adjuvants, and sorption promoters, and are collectively referred herein simply as "enhancers". These enhancers includes those with diverse mechanisms of action including those which have the function of improving the solubility and diffusibility of the active agent within the (B) compatibilizing agent and those which improve percutaneous absorption, for example, by changing the ability of the stratum corneum to retain moisture, softening the skin, improving the skin's permeability, acting as penetration assistants or hair-follicle openers or changing the state of the skin including the boundary layer. Some of these enhancers have more than one mechanism of action, but in essence they serve to enhance the delivery of the active agent to the substrate.

Some examples of enhancers are polyhydric alcohols such as dipropylene glycol, propylene glycol, and polyethylene glycol which enhance solubility of the active agent, oils such as olive oil, squalene, and lanolin; fatty ethers such as cetyl ether and oleyl ether; fatty acid esters such as isopropyl myristate which enhance diffusibility of the active agent; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the substrate, e.g. skin, and the active agents administered. Other agents include oleic and linoleic acids, ascorbic acid, panthenol, butylated hydroxytoluene, tocopherol, tocopheryl acetate, tocopheryl linoleate, propyl oleate, and isopropyl palmitate.

In certain embodiments of the invention, a plasticizer or tackifying agent may be incorporated into the system, typically into the composition, to improve the adhesive characteristics of the (B) compatibilizing agent. A tackifying agent is particularly useful in those embodiments in which the active agent does not plasticize the silicone polymer. Suitable tackifying agents are those known in the art including: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; and (7) hydrogenated wood rosins. The tackifying agent employed is typically compatible with the other components in the composition. Examples of suitable tackifying agents are silicone fluids (e.g., Q7-9120 Silicone Fluid, available from Dow Corning Corporation, Midland, Mich.), silicone resins (e.g., Q2-7466 INT, available from Dow Corning Corporation, Midland, Mich.), or mineral oil. Silicone fluids and silicone resins are useful for blends comprising polysiloxane as a major component. In other embodiments, where a synthetic rubber, for example, is a major component, mineral oil is a useful tackifying agent.

Notably some active agents, such as vasodilator nitroglycerin, function as plasticizers in the composition because they are soluble to a certain degree in the components of the composition. For active agents which are not readily soluble in the components, a co-solvent for the active agent and other components can be added. Co-solvents, such as lecithin, retinol derivatives, tocopherol, dipropylene glycol, triacetin, propylene glycol, saturated and unsaturated fatty acids, mineral oil, silicone fluid, alcohols, butyl benzyl phthalate, and the like are useful in the practice of the instant invention depending on the solubility of the active agent in the composition.

Independent of, or in conjunction with, the tackifying agent, the (B) compatibilizing agent may maintain contact between the system and the substrate. The (B) compatibilizing agent may be an adhesive that possesses sufficient tack and cohesive strength so that it can be adhered with mild pressure and also removed and the adhered again (to the same or another).

In addition to the above described plasticizers and tackifying agents, the (B) compatibilizing agent may include a variety of other formulation additives that are known in the art. These additives are typically included in small amounts to influence a select physical property or to improve a certain performance feature of the (B) compatibilizing agent. Examples of these additives include, but are not limited to, fillers, such as silicas or calcium carbonate, pigments, anti-oxidant agents, defoaming agents, wetting agents, and viscosity adjusting agents. These additives are applicable whether the (B) compatibilizing agent of the present invention is being used in a transdermal drug delivery system or not.

In one embodiment, the single phase formulation that resists phase separation comprises at least one of (A) the silicone, the acrylate, and combinations thereof. In this embodiment, the formulation also includes the (B) silicone acrylate hybrid compatibilizing agent that comprises silicone functionality and (meth)acrylate functionality and that is (or comprises) the reaction product of a silicon-containing pressure sensitive adhesive composition, and a (meth)acrylate monomer, in the presence of an initiator. Moreover, in this embodiment, the silicon-containing pressure sensitive adhesive composition comprises the condensation reaction product of the silicone resin, the silicone polymer, and the silicon-containing capping agent, optionally in the presence of a catalyst, e.g. a condensation catalyst, as described above. Furthermore in this embodiment, the silicone resin and the silicone polymer are reacted to form the pressure sensitive adhesive wherein the silicon-containing capping agent is introduced prior to, during, or after the silicone resin and the silicone polymer react. In addition, in this embodiment, the silicon-containing capping agent reacts with the pressure sensitive adhesive after the silicone resin and the silicone polymer have been condensation reacted to form the pressure sensitive adhesive, or the silicon-containing capping agent reacts in-situ with the silicone resin and the silicone polymer.

In additional embodiments, the formulation includes from about 10 to about 90, from about 20 to about 80, from about 30 to about 70, from about 40 to about 60, or about 50, weight percent of acrylate. Said differently, the formulation, as a whole, may have a weight percent of acrylate functionality, acrylate content, and/or acrylate groups having a weight percentage within one of the aforementioned ranges. Alternatively, or in addition, the formulation may include from about 10 to about 90, from about 20 to about 80, from about 30 to about 70, from about 40 to about 60, or about 50, weight percent of silicone. Said differently, the formulation, as a whole, may have a weight percent of silicone functionality, silicone content, and/or silicone groups (e.g. M, D, T, and/or Q units) having a weight percentage within one of the aforementioned ranges. In still another embodiment, the formulation, as a whole, has a weight percent of silicone functionality and/or groups of about 50 weight percent and a weight percent of acrylate functionality and/or groups of about 50 weight percent.

Referring back to the (B) compatibilizing agent itself, this component may also include from about 10 to about 90, from about 20 to about 80, from about 30 to about 70, from about 40 to about 60, or about 50, weight percent of acrylate, as described above. Similarly, this component may also include from about 10 to about 90, from about 20 to about 80, from about 30 to about 70, from about 40 to about 60, or about 50, weight percent of silicone, as described above. In one embodiment, the (B) compatibilizing agent itself has about 25 weight percent of silicone and about 75 weight percent of acrylate. In another embodiment, the (B) compatibilizing agent itself has about 25 weight percent of acrylate and about 75 weight percent of silicone. In still another embodiment, the (B) compatibilizing agent itself has about 50 weight percent of silicone and about 50 weight percent of acrylate. In other embodiments, the formulation includes an excipient, e.g. selected from the group of dipropylene glycol, oleic acid, oleyl alcohol, mineral oil, and combinations thereof. In even other embodiments, the formulation includes a pharmaceutically active agent, e.g. selected from the group of ketoprofen, estradiol, clonidine, and combinations thereof.

Aside from the transdermal drug delivery system described above which uses the (B) compatibilizing agent, there is a wide array of advantages associated with this (B) compatibilizing agent in a wide variety of applications that is not found by using solely a silicone-based PSA or an acrylate-based PSA. Some of the advantages include, but are not limited to, effective adherence to substrates with a broad range of surface energies, improved solubility of a broader range of drugs, a larger effective temperature use range as compared to a pure acrylate-based PSA, and lower potential cost when compared to a pure silicone-based PSA.

Other applications for the (B) compatibilizing agent include, but are not limited to, tapes, labels, notes, bandages, transdermal drug delivery systems (e.g. patches), lipstick, hair spray, hair fixatives, and other cosmetic products, transfer adhesives, laminating adhesives, surface priming, and vibration damping.

Several features of the present invention including, but not limited to, the pressure sensitive adhesive (i), the silicon-containing capping agent (ii), the second silicon-containing capping agent, and the features of the transdermal drug delivery system are also described in U.S. Provisional Patent Application Ser. No. 60/730,070, which was filed on Oct. 25, 2005, and PCT International Application No. PCT/US2006/041430, which was filed on Oct. 24, 2006, both of which are entitled "TRANSDERMAL DRUG DELIVERY SYSTEM WITH ACRYLATE OR METHACRYLATE FUNCTIONAL PRESSURE SENSITIVE ADHESIVE COMPOSITION" and the disclosures of which are both hereby incorporated by reference in their entirety.

EXAMPLES

A series of single phase formulations (Examples 1-60) are formed according to this invention. A series of comparative formulations (Comparative Examples 1-54), which phase separate, are also formed. These comparative formulations do not include any of the silicone acrylate hybrid composition of this invention.

After formation, each of the Examples and the Comparative Examples are allowed to stand for approximately one month at room temperature. During this time, the vials are periodically visually evaluated to determine if phase separation occurs. In the following Examples, if phase separation is indicated, the phase separation occurred in a time between 1 hour and 7 days. If phase separation is indicated as not occurring, then that evaluation is made after one month. Said differently, the Examples below which do not phase separate remain as a single phase after one month of standing at room temperature in the vials.

One or more of the following components may be used in the Examples.

Hybrid 1:

Hybrid 1 is formed using the following method. To a 16 ounce jar, 74.58 g of 2-EHA, 60.97 g of MA, 214.01 g of a silicon-containing pressure sensitive adhesive composition, 32.72 g of ethyl acetate solvent and 0.196 g Vazo® 67 are added to form a pre-reaction mixture.

The silicon-containing pressure sensitive adhesive composition used herein is 60% weight solids in ethyl acetate and is produced via a condensation reaction of a silanol endblocked polydimethylsiloxane (PDMS) with a silicate resin and that is endblocked with a silicon-containing capping agent. 2-EHA is an ethylenically unsaturated monomer, specifically 2-ethylhexyl acrylate commercially available from Aldrich. MA is an ethylenically unsaturated monomer, specifically methyl acrylate commercially available from Aldrich. Vazo® 67 is a free radical initiator, specifically 2,2'-azobis(methylbutyronitrile) commercially available from DuPont.

The materials in the pre-reaction mixture are allowed to stir 15 minutes until thoroughly homogeneous. After mixing, 86.93 g of the pre-reaction mixture and 263.0 g of ethyl acetate solvent are added to a 4-neck glass reactor equipped with a heating mantle, stirring blade/shaft, nitrogen purge, condenser with cooling water and a thermocouple. The remaining portion of the pre-reaction mixture is added to a separate pear-shaped glass reservoir. Heating and mixing is then begun on the mixture in the reactor. The reaction temperature is set at 78° C. As soon as the reaction temperature is achieved, the mixture is allowed to react for 65 minutes prior to adding more of the pre-reaction mixture to the reactor. Once 65 minutes elapses, the mixture in the reservoir is then added at a rate of 1.69 grams/minutes for 175 minutes using a metering pump until the mixture in the reservoir is finished. The mixture in the reactor is then reacted at 78° C. for an additional 498 minutes to form the hybrid. Upon completion, the hybrid is allowed to cool to room temperature before removing the hybrid from the reactor. The final product is opaque.

Hybrid 2:

Hybrid 2 is formed using the following method. To a 16 ounce jar, 75.93 g of 2-EHA, 50.55 g of MA, 201.5 g of a first capped compound described below, 28.5 g of ethyl acetate solvent and 0.183 g Vazo® 67 are added to form a pre-reaction mixture. The 2-EHA, MA, and Vazo® 67 are as described above.

The materials in the pre-reaction mixture are allowed to stir 15 minutes until thoroughly homogeneous. After mixing, 85.4 g of the pre-reaction mixture and 245.0 g of ethyl acetate solvent are added to a 4-neck glass reactor equipped with a heating mantle, stirring blade/shaft, nitrogen purge, condenser with cooling water and a thermocouple. The remaining portion of the pre-reaction mixture is added to a separate pear-shaped glass reservoir. Heating and mixing is then begun on the mixture in the reactor. The reaction temperature is set at 78° C. As soon as the reaction temperature is achieved, the mixture is allowed to react for 60 minutes prior to adding more of the pre-reaction mixture to the reactor. Once 60 minutes elapses, the mixture in the reservoir is then added at a rate of 1.51 grams/minutes for 180 minutes using a metering pump until the mixture in the reservoir is finished. The mixture in the reactor is then reacted at 78° C. for an additional 1140 minutes to form the hybrid. Upon completion, the hybrid is allowed to cool to room temperature before removing the hybrid from the reactor. The final product is opaque.

Hybrid 3:

Hybrid 3 is formed using the following method. To a 16 ounce jar, 44.0 g of 2-EHA, 44.0 g of MA, 140.51 g of a second capped compound also described below, 13.9 g of ethyl acetate solvent and 0.126 g Vazo® 67 are added to form a pre-reaction mixture. The 2-EHA, MA, and Vazo® 67 are as described above.

The materials in the pre-reaction mixture are allowed to stir 15 minutes until thoroughly homogeneous. After mixing, 56.03 g of the pre-reaction mixture and 162.5 g of ethyl acetate solvent are added to a 4-neck glass reactor equipped with a heating mantle, stirring blade/shaft, nitrogen purge, condenser with cooling water and a thermocouple. The remaining portion of the pre-reaction mixture is added to a separate pear-shaped glass reservoir. Heating and mixing is then begun on the mixture in the reactor. The reaction temperature is set at 78° C. As soon as the reaction temperature is achieved, the mixture is allowed to react for 60 minutes prior to adding more of the pre-reaction mixture to the reactor. Once 60 minutes elapses, the mixture in the reservoir is then added at a rate of 1.43 grams/minutes for 130 minutes using a metering pump until the mixture in the reservoir is finished. The mixture in the reactor is then reacted at 78° C. for an additional 570 minutes to form the hybrid. Upon completion, the hybrid is allowed to cool to room temperature before removing the hybrid from the reactor. The final product is opaque.

Hybrid 4:

Hybrid 4 is formed using the following method. To a 16 ounce jar, 75.62 g of 2-EHA, 51.4 g of MA, 198.01 g of a third capped compound also described below, 31.02 g of ethyl acetate solvent and 0.183 g Vazo® 67 are added to form a pre-reaction mixture. The 2-EHA, MA, and Vazo® 67 are as described above.

The materials in the pre-reaction mixture are allowed to stir 15 minutes until thoroughly homogeneous. After mixing, 90.06 g of the pre-reaction mixture and 245.0 g of ethyl acetate solvent are added to a 4-neck glass reactor equipped with a heating mantle, stirring blade/shaft, nitrogen purge, condenser with cooling water and a thermocouple. The remaining portion of the pre-reaction mixture is added to a separate pear-shaped glass reservoir. Heating and mixing is then begun on the mixture in the reactor. The reaction temperature is set at 78° C. As soon as the reaction temperature is achieved, the mixture is allowed to react for 60 minutes prior to adding more of the pre-reaction mixture to the reactor. Once 60 minutes elapses, the mixture in the reservoir is then added at a rate of 1.48 grams/minutes for 180 minutes using a metering pump until the mixture in the reservoir is finished. The mixture in the reactor is then reacted at 78° C. for an additional 1140 minutes to form the hybrid. Upon completion, the hybrid is allowed to cool to room temperature before removing the hybrid from the reactor. The final product is opaque.

Hybrid 5:

Hybrid 5 is formed using the following method. To a 16 ounce jar, 63.4 g of 2-EHA, 42.4 g of MA, 150.3 g of a fourth capped compound also described below, 26.6 g of ethyl acetate solvent and 0.152 g Vazo® 67 are added to form a pre-reaction mixture. The 2-EHA, MA, and Vazo® 67 are as described above.

Referring back to the pre-reaction mixture described above, the materials in this pre-reaction mixture are allowed to stir 15 minutes until thoroughly homogeneous. After mixing, 67.48 g of the pre-reaction mixture and 204.09 g of ethyl acetate solvent are added to a 4-neck glass reactor equipped with a heating mantle, stifling blade/shaft, nitrogen purge, condenser with cooling water and a thermocouple. The remaining portion of the pre-reaction mixture is added to a separate pear-shaped glass reservoir. Heating and mixing is then begun on the mixture in the reactor. The reaction temperature is set at 78° C. As soon as the reaction temperature is achieved, the mixture is allowed to react for 60 minutes prior to adding more of the pre-reaction mixture to the reactor. Once 60 minutes elapses, the mixture in the reservoir is then added at a rate of 1.27 grams/minutes for 170 minutes using a metering pump until the mixture in the reservoir is finished. The mixture in the reactor is then reacted at 78° C. for an additional 1150 minutes to form the hybrid. Upon completion, the hybrid is allowed to cool to room temperature before removing the hybrid from the reactor. The final product is opaque.

Hybrid 6:

Hybrid 6 is a silicone acrylate hybrid that is produced through a radical polymerization between a silicon-containing PSA, 2-ethylhexyl acrylate and methyl acrylate and is 42% solids in ethyl acetate. More specifically, Hybrid 6 is formed using 32.91% of the silicone-containing PSA, 14.00% of the 2-EHA, 7.54% of the methyl acrylate, 0.03% of Vazo 67, and 45.52% of ethyl acetate.

Hybrid 7:

Hybrid 7 is formed using the following method. To a 16 ounce jar, 88.5 g of 2-EHA, 48.0 g of MA, 213.53 g of the silicon-containing pressure sensitive adhesive composition used to form Hybrid 1, 32.72 g of ethyl acetate solvent and 0.197 g Vazo® 67 are added to form a pre-reaction mixture. The 2-EHA, MA, and Vazo® 67 are as described above.

The materials in the pre-reaction mixture are allowed to stir 15 minutes until thoroughly homogeneous. After mixing, 90.3 g of the pre-reaction mixture and 263.9 g of ethyl acetate solvent are added to a 4-neck glass reactor equipped with a heating mantle, stirring blade/shaft, nitrogen purge, condenser with cooling water and a thermocouple. The remaining portion of the pre-reaction mixture is added to a separate pear-shaped glass reservoir. Heating and mixing is then begun on the mixture in the reactor. The reaction temperature is set at 78° C. As soon as the reaction temperature is achieved, the mixture is allowed to react for 63 minutes prior to adding more of the pre-reaction mixture to the reactor. Once 63 minutes elapses, the mixture in the reservoir is then added at a rate of 1.49 grams/minutes for 197 minutes using a metering pump until the mixture in the reservoir is finished. The mixture in the reactor is then reacted at 78° C. for an additional 447 minutes to form the hybrid. Upon completion, the hybrid is allowed to cool to room temperature before removing the hybrid from the reactor. The final product is opaque.

Hybrid 8:

Hybrid 8 is formed using the following method. To a 16 ounce jar, 81.36 g of 2-EHA, 87.02 g of MA, 213.9 g of the silicon-containing pressure sensitive adhesive composition used to form Hybrid 1, 32.77 g of ethyl acetate solvent and 0.195 g Vazo® 67 are added to form a pre-reaction mixture. The materials in this pre-reaction mixture are allowed to stir 15 minutes until thoroughly homogeneous. After mixing, 92.1 g of the pre-reaction mixture and 263.4 g of ethyl acetate solvent are added to a 4-neck glass reactor equipped with a heating mantle, stirring blade/shaft, nitrogen purge, condenser with cooling water and a thermocouple. The remaining portion of the pre-reaction mixture is added to a separate pear-shaped glass reservoir. Heating and mixing is then begun on the mixture in the reactor. The reaction temperature is set at 78° C. As soon as the reaction temperature is achieved, the mixture is allowed to react for 60 minutes prior to adding more of the pre-reaction mixture to the reactor. Once 60 minutes elapses, the mixture in the reservoir is then added at a rate of 1.27 grams/minutes for 255 minutes using a metering pump until the mixture in the reservoir is finished. The mixture in the reactor is then reacted at 78° C. for an additional 437 minutes to form the hybrid. Upon completion, the hybrid is allowed to cool to room temperature before removing the hybrid from the reactor. The final product is opaque.

Hybrid 9:

Hybrid 9 is formed using the following method. To a 32 ounce jar, 682.9 g of 2-EHA, 682.6 g of MA, 2128.4 g of a silicon-containing pressure sensitive adhesive composition used to form Hybrid 1, and 353.6 g of ethyl acetate solvent are added to form pre-reaction mixture A. To a second 32 ounce jar, 1.987 g of Vazo® 67 and 822.41 g of ethyl acetate solvent are added to form pre-reaction mixture B. The 2-EHA, MA, silicon-containing pressure sensitive adhesive composition used to form Hybrid 1 and Vazo® 67 are as described above. Both A and B are allowed to stir 15 minutes until thoroughly homogeneous. After mixing, 1047.0 g of A, 206.0 g of B and 1831.2 g of ethyl acetate solvent are added to a 4-neck glass reactor equipped with a heating jacket, stirring blade/shaft, nitrogen purge, condenser with cooling water and a thermocouple. The remaining portions of A and B are added to separate pear-shaped glass reservoirs. Heating and mixing is then begun on the mixture in the reactor. The reaction temperature is set at 78° C. As soon as the reaction temperature is achieved, the mixture is allowed to react for 60 minutes prior to adding more of the pre-reaction mixtures to the reactor. Once 60 minutes elapses, the mixtures in the reservoirs are added to the reactor using metering pumps at a rate of 11.38 grams/min for A and 3.16 grams/min for B until the reservoirs are empty. The mixture in the reactor is reacted at 78° C. for an additional 1200 minutes. 79.69 g HMDZ and 2.49 g of trifluoroacetic acid are then added to the reactor and the mixture is reacted at 78° C. for an additional 240 minutes. 406.25 g of water and 82.1 g of isopropyl alcohol are then added to the reactor and the mixture is reacted at 78° C. for an additional 60 minutes. Following the final 60 minutes of reaction, the water and isopropyl alcohol is removed from the mixture by collection in a Dean-Starke trap. Upon completion, the Hybrid is allowed to cool to room temperature before removal from the reactor. The final product is opaque.

Formation of First Capped Compound:

The first capped compound is formed using the following method. Approximately 700 grams of Silicone 1, described below, is dried in a forced air oven at 150° C. for 120 minutes to remove ethyl acetate solvent. Then, 360.0 grams of the Silicone 1 and 240.0 grams of xylene are loaded into a 4-neck glass reactor equipped with a heating mantle, stifling blade/shaft, nitrogen purge, condenser with cooling water and a thermocouple. The components are allowed to mix until thoroughly homogeneous. 19.47 grams of HMDZ is then added to the reactor and heating is applied to the system. The reaction temperature is set at 115° C. Once the target temperature is reached, the mixture is allowed to react for 11.25 hours to ensure completion of the reaction. The contents of the reaction are allowed to cool to room temperature before removal from the reactor. The contents of the reaction are then dried in a forced air oven at 200° C. for 2 hours to remove the xylene solvent. 314.0 grams of the contents of the reaction and 190.0 grams of ethyl acetate are added to a 32 ounce jar and allowed to mix overnight on a mixing wheel until homogeneous. 470.0 grams of the solution and 2.89 grams of CA are added to a 16 ounce jar and the material is allowed to mix overnight on a mixing wheel. Generation of HCl is immediate as indicated by pH paper color change. The next day, 35.0 grams of sodium bicarbonate is added to aid in the neutralization of the HCl. The sample is allowed to mix overnight. The sample is then pressure filtered to remove particulate. The final product is clear. In this example, HMDZ is a silicon-containing capping agent which provides trimethylsiloxy functionality and is, more specifically, hexamethyldisilazane. In addition, in this example, CA is a silicon-containing capping agent and is, more specifically, 3-methacryloxypropyldimethyl-chlorosilane commercially available from Gelest.

Formation of Second Capped Compound:

The second capped compound is formed using the following method. Approximately 500 grams of Silicone 1, described both above and below, is dried in a forced air oven at 150° C. for 120 minutes to remove the ethyl acetate solvent. Then 180.71 grams of the dried silicone and 120.47 grams of xylene are loaded into a 4-neck glass reactor equipped with a heating mantle, stifling blade/shaft, nitrogen purge, condenser with cooling water and a thermocouple. The components are allowed to mix until thoroughly homogeneous. 9.74 grams of HMDZ, also described above, is then added to the reactor and heating is applied to the system. The reaction temperature is set at 115° C. Once the target temperature is reached, the mixture is allowed to react for 491 minutes to ensure completion of the reaction. The contents of the reaction are allowed to cool before removal from the reactor. The contents of the reaction are then dried in a forced air oven at 200° C. for 1.5 hours to remove the xylene solvent. 174.33 grams of the contents of the reaction and 116.30 grams of ethyl acetate are added to a 16 ounce jar and allowed to mix overnight on a mixing wheel until homogeneous. 259.71 grams of the solution and 1.58 grams of CA, also described above, are added to a 3-neck flask equipped with a stirring blade/shaft, nitrogen purge, condenser with cooling water and a thermocouple and allowed to mix for 24 hours. Generation of HCl is immediate as indicated by pH paper color change. 50.0 grams of sodium bicarbonate is added to the flask to aid in the neutralization of the HCl. The sample is allowed to mix for 21 hours. The sample is then pressure filtered to remove particulate. The final product is clear.

Formation of Third Capped Compound:

The third capped compound is formed using the following method. Approximately 700 grams of Silicone 1, described both above and below, is dried in a forced air oven at 150° C. for 120 minutes to remove the ethyl acetate solvent. Then 360.0 grams of the dried silicone and 240.0 grams of xylene are loaded into a 4-neck glass reactor equipped with a heating mantle, stirring blade/shaft, nitrogen purge, condenser with cooling water and a thermocouple. The components are allowed to mix until thoroughly homogeneous. 23.76 grams of HMDZ is then added to the reactor and heating is applied to the system. The reaction temperature is set at 115° C. Once the target temperature is reached, the mixture is allowed to react for 11.25 hours to ensure completion of the reaction. The contents of the reaction are allowed to cool to room temperature before removal from the reactor. The contents of the reaction are then dried in a forced air oven at 200° C. for 2 hours to remove the xylene solvent. 300.87 grams of the contents of the reaction and 178.0 grams of ethyl acetate are added to a 32 ounce jar and allowed to mix overnight on a mixing wheel until homogeneous. 429.0 grams of the solution and 2.61 grams of CA are added to a 16 ounce jar and the material is allowed to mix overnight on a mixing wheel. Generation of HCl is immediate as indicated by pH paper color change. The next day, 35.0 grams of sodium bicarbonate is added to aid in the neutralization of the HCl. The sample is allowed to mix overnight. The sample is then pressure filtered to remove particulate. The final product is clear. The HMDZ and CA are as described above.

Formation of Fourth Capped Compound:

The fourth capped compound is formed using the following method. Approximately 700 grams of Silicone 1, described both above and below, is dried in a forced air oven at 150° C. for 120 minutes to remove the ethyl acetate solvent. Then 360.0 grams of the dried silicone and 240.0 grams of xylene are loaded into a 4-neck glass reactor equipped with a heating mantle, stirring blade/shaft, nitrogen purge, condenser with cooling water and a thermocouple. The components are allowed to mix until thoroughly homogeneous. 15.20 grams of HMDZ is then added to the reactor and heating is applied to the system. The reaction temperature is set at 115° C. Once the target temperature is reached, the mixture is allowed to react for 11.25 hours to ensure completion of the reaction. The contents of the reaction are allowed to cool to room temperature before removal from the reactor. The contents of the reaction are then dried in a forced air oven at 200° C. for 2 hours to remove the xylene solvent. 308.0 grams of the contents of the reaction and 185.0 grams of ethyl acetate are added to a 32 ounce jar and allowed to mix overnight on a mixing wheel until homogeneous. 459.0 grams of the solution and 2.79 grams of CA are added to a 16 ounce jar and the material is allowed to mix overnight on a mixing wheel. Generation of HCl is immediate as indicated by pH paper color change. The next day, 35.0 grams of sodium bicarbonate is added to aid in the neutralization of the HCl. The sample is allowed to mix overnight. The sample is then pressure filtered to remove particulate. The final product is clear. The HMDZ and CA are as described above.

Silicone 1, first introduced above, is a conventional, i.e., uncapped, silicone PSA that is produced through a condensation reaction of a silanol endblocked polydimethylsiloxane (PDMS) with a silicate resin and is 60% weight solids in ethyl acetate.

Silicone 2, which is utilized in the Examples below, is formed using the following method. Approximately 1000 grams of Silicone 1 is dried in a forced air oven at 150° C. for 120 minutes to remove the ethyl acetate solvent. Then, 506.2 grams of dried Silicone 1 and 338.3 grams of xylene are loaded into a 4-neck glass reactor equipped with a heating mantle, stirring blade/shaft, nitrogen purge, condenser with cooling water and a thermocouple. The components are allowed to mix until thoroughly homogeneous. 111.0 grams of HMDZ is then added to the reactor and heating is applied to the system. The reaction temperature is set at 145° C. As soon as a solvent reflux is achieved, the mixture is allowed to reflux for 15 hours to ensure completion of the reaction. The adhesive is allowed to cool to room temperature before removal from the reactor. The adhesive is then dried in a forced air oven at 80° C. for 11.5 hours to remove the xylene solvent. The resulting adhesive solids are then resolvated in ethyl acetate at 60% solids. The final product is clear.

Acrylate 1, which is also utilized in the Examples below, is Gelva 3083 that is commercially available from Cytec Industries Inc of Woodland Park, N.J.

Copolymer is VA 64 commercially available from BASF Corporation.

Formation of Examples 1-60 and Comparative Examples 1-54:

Each of Examples 1-60 is formed by adding one of the aforementioned hybrids into a vial. Subsequently, Silicone 1 and/or 2 or Acrylate 1 is also added to the vial. One or more excipients and/or pharmaceutically active agents is also added, dependent on Example. Additionally, ethyl acetate is added, if needed, to adjust a percent solids to between 45% and 50% solids. Then, each vial is blended using a process rotator to ensure mixing. The weight percentages of the hybrids, the silicones and acrylates, the excipients, and pharmaceutically active agents are set forth in the Tables below.

Each of the Comparative Examples 1-54 is formed by adding Silicone 1 and/or 2 or Acrylate 1 to a vial without any of the hybrids. The same one or more excipients and/or pharmaceutically active agents is also added, dependent on Example. Ethyl acetate, if needed, is then added to adjust a percent solids to between 45% and 50% solids. Then, each vial is blended using a process rotator to ensure mixing. The weight percentages of the hybrids, the silicones and acrylates, the excipients, and pharmaceutically active agents are set forth in the Tables below.

After formation, each of the Examples and the Comparative Examples are allowed to stand as described above, after which each is visually evaluated to determine whether phase separation occurs. The data associated with the visual evaluations is set forth in the Tables below.

TABLE 1

|  | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Hybrid 1 | 50 | 20 | 50 | 20 | — | — | — | — | — | — |
| Hybrid 2 | — | — | — | — | 50 | 20 | 50 | 20 | — | — |
| Hybrid 3 | — | — | — | — | — | — | — | — | 50 | 20 |
| Hybrid 4 | — | — | — | — | — | — | — | — | — | — |
| Hybrid 5 | — | — | — | — | — | — | — | — | — | — |
| Hybrid 6 | — | — | — | — | — | — | — | — | — | — |
| Silicone 1 | 50 | 80 | — | — | 50 | 80 | — | — | 50 | 80 |
| Silicone 2 | — | — | 50 | 80 | — | — | 50 | 80 | — | — |
| Acrylate 1 | — | — | — | — | — | — | — | — | — | — |
| Phase Separation | No | No | No | No | No | No | No | No | No | No |

|  | Ex. 11 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|
| Hybrid 1 | — | — | — | — | — | — | — | — | — | — |
| Hybrid 2 | — | — | — | 50 | — | — | — | — | — | — |
| Hybrid 3 | 50 | 20 | 50 | — | — | — | — | — | — | — |
| Hybrid 4 | — | — | — | — | 50 | 20 | 50 | 20 | — | — |
| Hybrid 5 | — | — | — | — | — | — | — | — | 50 | 20 |
| Hybrid 6 | — | — | — | — | — | — | — | — | — | — |
| Silicone 1 | — | — | — | — | 50 | 80 | — | — | 50 | 80 |
| Silicone 2 | 50 | 80 | — | — | — | — | 50 | 80 | — | — |
| Acrylate 1 | — | — | 50 | 50 | — | — | — | — | — | — |
| Phase Separation | No | No | No | Yes | No | No | No | No | No | No |

|  | Ex. 21 | Ex. 22 | Ex. 23 | Ex. 24 | Ex. 25 | Ex. 26 | Ex. 27 | Ex. 28 | Ex. 29 |
|---|---|---|---|---|---|---|---|---|---|
| Hybrid 1 | — | — | — | — | — | — | — | — | — |
| Hybrid 2 | — | — | — | — | — | — | — | — | — |
| Hybrid 3 | — | — | — | — | — | — | — | — | — |
| Hybrid 4 | — | — | — | — | — | — | 50 | — | — |
| Hybrid 5 | 50 | 20 | — | — | — | — | — | 50 | — |
| Hybrid 6 | — | — | 50 | 20 | 50 | 20 | — | — | 50 |
| Silicone 1 | — | — | 50 | 80 | — | — | — | — | — |
| Silicone 2 | 50 | 80 | — | — | 50 | 80 | — | — | — |
| Acrylate 1 | — | — | — | — | — | — | 50 | 50 | 50 |
| Phase Separation | No | No | No | No | No | No | No | No | No |

|  | Comp Ex. 1 | Comp Ex. 2 | Comp Ex. 3 | Comp Ex. 4 | Comp Ex. 5 |
|---|---|---|---|---|---|
| Hybrid 1 | — | — | — | — | — |
| Hybrid 2 | — | — | — | — | — |
| Hybrid 3 | — | — | — | — | — |
| Hybrid 4 | — | — | — | — | — |
| Hybrid 5 | — | — | — | — | — |
| Hybrid 6 | — | — | — | — | — |
| Silicone 1 | 10 | 25 | 50 | 75 | 90 |
| Silicone 2 | — | — | — | — | — |
| Acrylate 1 | 90 | 75 | 50 | 25 | 10 |
| Phase Separation | Yes | Yes | Yes | Yes | Yes |

|  | Comp Ex. 6 | Comp Ex. 7 | Comp Ex. 8 | Comp Ex. 9 | Comp Ex. 10 |
|---|---|---|---|---|---|
| Hybrid 1 | — | — | — | — | — |
| Hybrid 2 | — | — | — | — | — |
| Hybrid 3 | — | — | — | — | — |
| Hybrid 4 | — | — | — | — | — |

TABLE 1-continued

|  |  |  |  |  |  |
|---|---|---|---|---|---|
| Hybrid 5 | — | — | — | — | — |
| Hybrid 6 | — | — | — | — | — |
| Silicone 1 | — | — | — | — | — |
| Silicone 2 | 10 | 25 | 50 | 75 | 90 |
| Acrylate 1 | 90 | 75 | 50 | 25 | 10 |
| Phase Separation | Yes | Yes | Yes | Yes | Yes |

TABLE 2

|  | Ex. 30 | Ex. 31 | Ex. 32 | Ex. 33 | Ex. 34 | Ex. 35 |
|---|---|---|---|---|---|---|
| Hybrid 2 | 46.25 | 46.25 | 46.25 | 46.25 | 46.25 | 46.25 |
| Acrylate 1 | — | — | — | — | — | — |
| Silicone 1 | 46.25 | 46.25 | 46.25 | — | — | — |
| Silicone 2 | — | — | — | 46.25 | 46.25 | 46.25 |
| Excipient 1 | 7.5 | — | — | 7.5 | — | — |
| Excipient 2 | — | 7.5 | — | — | 7.5 | — |
| Excipient 3 | — | — | 7.5 | — | — | 7.5 |
| Phase Separation | No | No | No | No | No | No |

|  | Comp Ex. 11 | Comp Ex. 12 | Comp Ex. 13 | Comp Ex. 14 |
|---|---|---|---|---|
| Hybrid 2 | — | — | — | — |
| Acrylate 1 | 48.75 | 24.38 | 9.75 | 46.25 |
| Silicone 1 | 48.75 | 73.12 | 87.75 | 46.25 |
| Silicone 2 | — | — | — | — |
| Excipient 1 | 2.5 | 2.5 | 2.5 | 7.5 |
| Excipient 2 | — | — | — | — |
| Excipient 3 | — | — | — | — |
| Phase Separation | Yes | Yes | Yes | Yes |

|  | Comp Ex. 15 | Comp Ex. 16 | Comp Ex. 17 | Comp Ex. 18 | Comp Ex. 19 |
|---|---|---|---|---|---|
| Hybrid 2 | — | — | — | — | — |
| Acrylate 1 | 23.13 | 9.25 | 48.75 | 24.38 | 9.75 |
| Silicone 1 | 69.37 | 83.25 | 48.75 | 73.12 | 87.75 |
| Silicone 2 | — | — | — | — | — |
| Excipient 1 | 7.5 | 7.5 | — | — | — |
| Excipient 2 | — | — | 2.5 | 2.5 | 2.5 |
| Excipient 3 | — | — | — | — | — |
| Phase Separation | Yes | Yes | Yes | Yes | Yes |

|  | Comp Ex. 20 | Comp Ex. 21 | Comp Ex. 22 | Comp Ex. 23 | Comp Ex. 24 |
|---|---|---|---|---|---|
| Hybrid 2 | — | — | — | — | — |
| Acrylate 1 | 46.25 | 23.13 | 9.25 | 48.75 | 24.38 |
| Silicone 1 | 46.25 | 69.37 | 83.25 | 48.75 | 73.12 |
| Silicone 2 | — | — | — | — | — |
| Excipient 1 | — | — | — | — | — |
| Excipient 2 | 7.5 | 7.5 | 7.5 | — | — |
| Excipient 3 | — | — | — | 2.5 | 2.5 |
| Phase Separation | Yes | Yes | Yes | Yes | Yes |

|  | Comp Ex. 25 | Comp Ex. 26 | Comp Ex. 27 | Comp Ex. 28 | Comp Ex. 29 |
|---|---|---|---|---|---|
| Hybrid 2 | — | — | — | — | — |
| Acrylate 1 | 9.75 | 46.25 | 23.13 | 9.25 | 46.25 |
| Silicone 1 | 87.75 | 46.25 | 69.37 | 83.25 | 46.25 |
| Silicone 2 | — | — | — | — | — |
| Excipient 1 | — | — | — | — | 7.5 |
| Excipient 2 | — | — | — | — | — |
| Excipient 3 | 2.5 | 7.5 | 7.5 | 7.5 | — |
| Phase Separation | Yes | Yes | Yes | Yes | Yes |

TABLE 2-continued

|  | Comp Ex. 30 | Comp Ex. 31 | Comp Ex. 32 | Comp Ex. 33 | Comp Ex. 34 |
|---|---|---|---|---|---|
| Hybrid 2 | — | — | — | — | — |
| Acrylate 1 | 18.5 | 46.25 | 18.5 | 46.25 | 18.5 |
| Silicone 1 | 74 | 46.25 | 74 | 46.25 | 74 |
| Silicone 2 | — | — | — | — | — |
| Excipient 1 | 7.5 | — | — | — | — |
| Excipient 2 | — | 7.5 | 7.5 | — | — |
| Excipient 3 | — | — | — | 7.5 | 7.5 |
| Phase Separation | Yes | Yes | Yes | Yes | Yes |

|  | Comp Ex. 35 | Comp Ex. 36 | Comp Ex. 37 | Comp Ex. 38 | Comp Ex. 39 | Comp Ex. 40 |
|---|---|---|---|---|---|---|
| Hybrid 2 | — | — | — | — | — | — |
| Acrylate 1 | 48.75 | 19.5 | 48.75 | 19.5 | 48.75 | 19.5 |
| Silicone 1 | 48.75 | 78 | 48.75 | 78 | 48.75 | 78 |
| Silicone 2 | — | — | — | — | — | — |
| Excipient 1 | 2.5 | 2.5 | — | — | — | — |
| Excipient 2 | — | — | 2.5 | 2.5 | — | — |
| Excipient 3 | — | — | — | — | 2.5 | 2.5 |
| Phase Separation | Yes | Yes | Yes | Yes | Yes | Yes |

TABLE 3

|  | Ex. 36 | Ex. 37 | Comp Ex. 41 | Comp Ex. 42 | Comp Ex. 43 |
|---|---|---|---|---|---|
| Hybrid 7 | 35 | 14 | — | — | — |
| Acrylate 1 | — | — | 35 | 17.5 | 7 |
| Silicone 1 | 35 | 56 | 35 | 52.5 | 63 |
| Excipient 3 | 10 | 10 | 10 | 10 | 10 |
| Copolymer | 10 | 10 | 10 | 10 | 10 |
| Ketoprofen | 10 | 10 | 10 | 10 | 10 |
| Phase Separation | No | No | Yes | Yes | Yes |

TABLE 4

|  | Comp Ex. 44 | Comp Ex. 45 | Comp Ex. 46 | Comp Ex. 47 |
|---|---|---|---|---|
| Acrylate 1 | 48.25 | 24.125 | 9.65 | 47.5 |
| Silicone 2 | 48.25 | 72.35 | 86.85 | 47.5 |
| Excipient 1 | 2.5 | 2.5 | 2.5 | 2.5 |
| Clonidine | 1 | 1 | 1 | 2.5 |
| Phase Separation | Yes | Yes | Yes | Yes |

TABLE 5

|  | Ex. 38 | Ex. 39 | Comp Ex. 48 | Comp Ex. 49 | Comp Ex. 50 |
|---|---|---|---|---|---|
| Hybrid 8 | 38 | 15.2 | — | — | — |
| Acrylate 1 | — | — | 38 | 19 | 7.6 |
| Silicone 1 | 38 | 60.8 | 38 | 57 | 68.4 |
| Excipient 2 | 9 | 9 | 9 | 9 | 9 |
| Excipient 4 | 6 | 6 | 6 | 6 | 6 |
| Copolymer | 7.5 | 7.5 | 7.5 | 7.5 | 7.5 |

TABLE 5-continued

|  | Ex. 38 | Ex. 39 | Comp Ex. 48 | Comp Ex. 49 | Comp Ex. 50 |
|---|---|---|---|---|---|
| Estradiol | 1.5 | 1.5 | 1.5 | 1.5 | 1.5 |
| Phase Separation | No | No | Yes | Yes | Yes |

TABLE 6

|  | Ex. 40 | Ex. 41 | Ex. 42 | Comp Ex. 51 | Comp Ex. 52 | Comp Ex. 53 | Comp Ex. 54 |
|---|---|---|---|---|---|---|---|
| Hybrid 3 | 38 | 38.25 | 38.5 | — | — | — | — |
| Acrylate 1 | — | — | — | 38 | 19 | 19.13 | 19.25 |
| Silicone 2 | 38 | 38.25 | 38.5 | 38 | 57 | 57.37 | 57.75 |
| Excipient 2 | 9 | 9 | 9 | 9 | 9 | 9 | 9 |
| Excipient 4 | 6 | 6 | 6 | 6 | 6 | 6 | 6 |
| Copolymer | 7.5 | 7.5 | 7.5 | 7.5 | 7.5 | 7.5 | 7.5 |
| Estradiol | 1.5 | 1 | 0.5 | 1.5 | 1.5 | 1 | 0.5 |
| Phase Separation | No | No | No | Yes | Yes | Yes | Yes |

TABLE 7

|  | Ex. 43 | Ex. 44 | Ex. 45 | Ex. 46 | Ex. 47 | Ex. 48 |
|---|---|---|---|---|---|---|
| Hybrid 9 | 50 | 46.25 | 46.25 | 46.25 | 50 | 46.25 |
| Acrylate 1 | 50 | 46.25 | 46.25 | 46.25 | — | — |
| Silicone 2 | — | — | — | — | 50 | 46.25 |
| Excipient 1 | — | 7.5 | — | — | — | 7.5 |
| Excipient 2 | — | — | 7.5 | — | — | — |
| Excipient 3 | — | — | — | 7.5 | — | — |
| Phase Separation | No | No | No | No | No | No |

|  | Ex. 49 | Ex. 50 | Ex. 51 | Ex. 52 | Ex. 53 | Ex. 54 |
|---|---|---|---|---|---|---|
| Hybrid 9 | 46.25 | 46.25 | 20 | 18.5 | 18.5 | 18.5 |
| Acrylate 1 | — | — | — | — | — | — |
| Silicone 2 | 46.25 | 46.25 | 80 | 74.0 | 74.0 | 74.0 |
| Excipient 1 | — | — | — | 7.5 | — | — |
| Excipient 2 | 7.5 | — | — | — | 7.5 | — |
| Excipient 3 | — | 7.5 | — | — | — | 7.5 |
| Phase Separation | No | No | No | No | No | No |

TABLE 8

|  | Ex. 55 | Ex. 56 | Ex. 57 |
|---|---|---|---|
| Hybrid 9 | 38 | 15.2 | 38 |
| Acrylate 1 | — | — | 38 |
| Silicone 2 | 38 | 60.8 | — |
| Excipient 2 | 9 | 9 | 9 |
| Excipient 4 | 6 | 6 | 6 |
| Copolymer | 7.5 | 7.5 | 7.5 |
| Estradiol | 1.5 | 1.5 | 1.5 |
| Phase Separation | No | No | No |

TABLE 9

|  | Ex. 58 | Ex. 59 | Ex. 60 |
|---|---|---|---|
| Hybrid 9 | 35 | 14 | 35 |
| Acrylate 1 | — | — | 35 |
| Silicone 2 | 35 | 56 | — |
| Excipient 3 | 10 | 10 | 10 |
| Copolymer | 10 | 10 | 10 |
| Ketoprofen | 10 | 10 | 10 |
| Phase Separation | No | No | No |

The data set forth above indicates that the single phase formulation of this invention resists phase separation as compared to the comparative examples. More specifically, each of the comparative examples phase separates after short amounts of time (e.g. 1 hour to 7 days) while the inventive examples tend to resist phase separation after one month of resting at room temperature. Even more specifically, the inventive examples remain in a single phase even using multiple pharmaceutically active agents and excipients. Conversely, the comparative examples tend to phase separate which, as described above, can cause many problems during creation, storage, and use of the formulations.

One or more of the values described above may vary by ±5%, ±10%, ±15%, ±20%, ±25%, etc. so long as the variance remains within the scope of the disclosure. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both singly and multiply dependent, is herein expressly contemplated. The disclosure is illustrative including words of description rather than of limitation. Many modifications and variations of the present disclosure are possible in light of the above teachings, and the disclosure may be practiced otherwise than as specifically described herein.

What is claimed is:

1. A single phase silicone acrylate formulation that resists phase separation and comprises:
   A. at least one of a silicone pressure sensitive adhesive composition, an acrylic pressure sensitive adhesive composition, and combinations thereof; and
   B. a silicone acrylate hybrid compatibilizing agent comprising silicone functionality and (meth)acrylate functionality and that is the reaction product of;
      (1) a silicon-containing pressure sensitive adhesive composition, and
      (2) a (meth)acrylate monomer, in the presence of
      (3) an initiator,
   wherein said (1) silicon-containing pressure sensitive adhesive composition comprises the condensation reaction product of;
      (a) a silicone resin,
      (b) a silicone polymer, and
      (c) a silicon-containing capping agent,
         optionally in the presence of a catalyst,
   wherein said (a) silicone resin and said (b) silicone polymer are reacted to form a pressure sensitive adhesive,
   wherein said (c) silicon-containing capping agent is introduced prior to, during, or after said (a) silicone resin and (b) silicone polymer react, and
   wherein;
   said (c) silicon-containing capping agent reacts with said pressure sensitive adhesive after said (a) silicone resin and said (b) silicone polymer have been condensation reacted to form said pressure sensitive adhesive, or
   said (c) silicon-containing capping agent reacts in-situ with said (a) silicone resin and said (b) silicone polymer.

2. A single phase formulation according to claim 1 comprising from about 10 to about 90 weight percent of acrylate content.

3. A single phase formulation according to claim 2 comprising from about 10 to about 90 weight percent of silicone content.

4. A single phase formulation according to claim 1 comprising from about 10 to about 90 weight percent of silicone content.

5. A single phase formulation according to claim 1 wherein said silicone acrylate hybrid compatibilizing agent comprises about 50 weight percent of silicone content and about 50 weight percent of (meth)acrylate content.

6. A single phase formulation according to claim 1 wherein said silicone acrylate hybrid compatibilizing agent comprises about 25 weight percent of silicone content and about 75 weight percent of (meth)acrylate content.

7. A single phase formulation according to claim 1 wherein said silicone acrylate hybrid compatibilizing agent comprises about 75 weight percent of silicone content and about 25 weight percent of (meth)acrylate content.

8. A single phase formulation according to claim 1 further comprising an excipient.

9. A single phase formulation according to claim 8 wherein said excipient is selected from the group of dipropylene glycol, oleic acid, oleyl alcohol, mineral oil, and combinations thereof.

10. A single phase formulation according to claim 1 further comprising a pharmaceutically active agent.

11. A single phase formulation according to claim 10 wherein said pharmaceutically active agent is selected from the group of ketoprofen, estradiol, clonidine, and combinations thereof.

12. A single phase formulation according to claim 1 wherein said (A) silicone pressure sensitive adhesive composition is the condensation reaction product of a silanol end-blocked polydimethylsiloxane and a silicate resin.

13. A single phase formulation according to claim 12 wherein said polydimethylsiloxane and/or said silicate resin is capped with trimethylsiloxy functionality.

14. A single phase formulation according to claim 1 wherein said (A) acrylic pressure sensitive adhesive composition is formed from the polymerization of 2-ethylhexyl acrylate and methylacrylate.

15. A single phase silicone acrylate formulation that resists phase separation and comprises:
   A. at least one of a silicone pressure sensitive adhesive composition, an acrylic pressure sensitive adhesive composition, and combinations thereof; and
   B. a silicone acrylate hybrid compatibilizing agent comprising silicone functionality and (meth)acrylate functionality and that is the reaction product of;
      (1) a silicon-containing pressure sensitive adhesive composition, and
      (2) a (meth)acrylate monomer, in the presence of
      (3) an initiator,
   wherein said (1) silicon-containing pressure sensitive adhesive composition comprises the condensation reaction product of;
      (a) a silicone resin,
      (b) a silicone polymer, and
      (c) a silicon-containing capping agent,
         optionally in the presence of a catalyst,
      wherein said (a) silicone resin and said (b) silicone polymer are reacted to form a pressure sensitive adhesive,
      wherein said (c) silicon-containing capping agent is introduced prior to, during, or after said (a) silicone resin and (b) silicone polymer react, and
      wherein;
         said (c) silicon-containing capping agent reacts with said pressure sensitive adhesive after said (a) silicone resin and said (b) silicone polymer have been condensation reacted to form said pressure sensitive adhesive, or
         said (c) silicon-containing capping agent reacts in-situ with said (a) silicone resin and said (b) silicone polymer,
   C. an excipient selected from the group of dipropylene glycol, oleic acid, oleyl alcohol, mineral oil, and combinations thereof, and
   D. a pharmaceutically active agent,
   wherein said single phase formulation comprises about 10 to about 90 weight percent of acrylate content and from about 10 to about 90 weight percent of silicone content.

16. A single phase formulation according to claim 15 comprising from about 10 to about 90 weight percent of acrylate content.

17. A single phase formulation according to claim 16 comprising from about 10 to about 90 weight percent of silicone content.

18. A single phase formulation according to claim 15 comprising from about 10 to about 90 weight percent of silicone content.

19. A single phase formulation according to claim 15 wherein said silicone acrylate hybrid compatibilizing agent comprises about 50 weight percent of silicone content and about 50 weight percent of (meth)acrylate content.

20. A single phase formulation according to claim 15 wherein said silicone acrylate hybrid compatibilizing agent comprises about 25 weight percent of silicone content and about 75 weight percent of (meth)acrylate content.

21. A single phase formulation according to claim 15 wherein said silicone acrylate hybrid compatibilizing agent comprises about 75 weight percent of silicone content and about 25 weight percent of (meth)acrylate content.

22. A single phase formulation according to claim 15 wherein said pharmaceutically active agent is selected from the group of ketoprofen, estradiol, clonidine, and combinations thereof.

23. A single phase formulation according to claim 15 wherein said (A) silicone pressure sensitive adhesive composition is the condensation reaction product of a silanol end-blocked polydimethylsiloxane and a silicate resin.

24. A single phase formulation according to claim 23 wherein said polydimethylsiloxane and/or said silicate resin is capped with trimethylsiloxy functionality.

25. A single phase formulation according to claim 15 wherein said (A) acrylic pressure sensitive adhesive composition is formed from the polymerization of 2-ethylhexyl acrylate and methylacrylate.

26. A method of minimizing phase separation of a single phase silicone acrylate formulation that comprises (A) at least one of a silicone pressure sensitive adhesive composition, an acrylic pressure sensitive adhesive composition, and combinations thereof and (B) a silicone acrylate hybrid compatibilizing agent comprising silicone functionality and (meth)acrylate functionality, said method comprising the step of combining (A) and (B) to form the single phase silicone acrylate formulation wherein the (B) silicone acrylate hybrid compatibilizing agent is the reaction product of;
   (1) a silicon-containing pressure sensitive adhesive composition, and
   (2) a (meth)acrylate monomer, in the presence of
   (3) an initiator,
   wherein the (1) silicon-containing pressure sensitive adhesive composition comprises the condensation reaction product of;
      (a) a silicone resin,
      (b) a silicone polymer, and
      (c) a silicon-containing capping agent,
         optionally in the presence of a catalyst,
      wherein the (a) silicone resin and the (b) silicone polymer are reacted to form a pressure sensitive adhesive, wherein the (c) silicon-containing capping agent is introduced prior to, during, or after the (a) silicone resin and (b) silicone polymer react, and wherein;

the (c) silicon-containing capping agent reacts with the pressure sensitive adhesive after the (a) silicone resin and the (b) silicone polymer have been condensation reacted to form the pressure sensitive adhesive, or the (c) silicon-containing capping agent reacts in-situ with the (a) silicone resin and the (b) silicone polymer.

27. A method according to claim 26 wherein the single phase silicone acrylate formulation further comprises an excipient selected from the group of dipropylene glycol, oleic acid, oleyl alcohol, mineral oil, and combinations thereof.

28. A method according to claim 26 wherein the (A) silicone pressure sensitive adhesive composition is the condensation reaction product of a silanol endblocked polydimethylsiloxane and a silicate resin.

29. A method according to claim 26 wherein the polydimethylsiloxane and/or the silicate resin is capped with trimethylsiloxy functionality.

30. A method according to claim 26 wherein the (A) acrylic pressure sensitive adhesive composition is formed from the polymerization of 2-ethylhexyl acrylate and methylacrylate.

* * * * *